(12) United States Patent
Hassan et al.

(10) Patent No.: US 7,351,427 B2
(45) Date of Patent: Apr. 1, 2008

(54) PHARMACEUTICAL COMPOSITION, A METHOD OF PREPARING IT AND A METHOD OF TREATMENT BY USE THEREOF

(75) Inventors: Zuzana Hassan, Huddinge (SE); Moustapha Hassan, Huddinge (SE)

(73) Assignee: Busulipo AB, Stockholm (SE)

( * ) Notice: Subject to any disclaimer, the term of this patent is extended or adjusted under 35 U.S.C. 154(b) by 458 days.

(21) Appl. No.: 10/425,980

(22) Filed: Apr. 30, 2003

(65) Prior Publication Data

US 2004/0022841 A1   Feb. 5, 2004

Related U.S. Application Data

(63) Continuation-in-part of application No. 09/719,840, filed as application No. PCT/SE99/01093 on Jun. 17, 1999, now abandoned.

(60) Provisional application No. 60/376,533, filed on May 1, 2002, provisional application No. 60/089,759, filed on Jun. 18, 1998.

(30) Foreign Application Priority Data

Jun. 18, 1919   (SE)   ..................... 9802197

(51) Int. Cl.
*A61K 9/127*   (2006.01)
*A61K 38/00*   (2006.01)
(52) U.S. Cl. ................ 424/450; 514/18; 514/517; 514/518; 514/527
(58) Field of Classification Search .................... None
See application file for complete search history.

(56) References Cited

U.S. PATENT DOCUMENTS

| 5,430,057 A | 7/1995 | Andersson et al. |
| 5,559,148 A | 9/1996 | Andersson et al. |

FOREIGN PATENT DOCUMENTS

| EP | 0546951 A1 * | 11/1992 |
| EP | 0 546 951 A1 | 6/1993 |
| WO | WO 86/01102 A1 | 2/1986 |
| WO | WO 88/06442 A1 | 9/1988 |
| WO | WO 90/14105 A1 | 11/1990 |
| WO | WO 92/22298 A1 | 12/1992 |
| WO | WO 9222298 A1 * | 12/1992 |
| WO | WO 95/08991 A1 | 4/1995 |

OTHER PUBLICATIONS

Muldoon et al. Rescue from Enhanced Alkylator-Induced Cell Death with Low Molecular Weight Sulfur-Containing Chemoprotectants. J. Pharm. Exp. Ther., 296; 797-805, 2001.*
Addison et al (The effect of cysteine on the immunosuppressive activity of busulphan, cyclophosphamide and nitrogen mustard, British Journal of Cancer. Mar. 1971; 25(1):172-81.*
Bandini et al "Toxicity Of High-Dose Bulsulphan And Cyclophosphamide As Conditioning Therapy For Allogenic Bone Marrow Transplantation In Adults With Haematological Malignancies", Bone Marrow Transplantation, 1994, vol. 13, pp. 577-581.
Bangham et al, "Diffusion Of Univalent Ions Across The Lamellae Of Swollen Phospholipids", J. Mol. Biol., 1995, vol. 13, pp. 238-252.
Bearman et al, "Regimen-Related Toxicity In Patients Undergoing Bone Marrow Transplantation", Journal of Clinical Oncology, Oct. 1988, vol. 6, No. 10, pp. 1562-1568.
Bearman, Scott, "The Syndrome Of Hepatic Veno-Occlusive Disease After Marrow Transplantation", BLOOD, 1995, vol. 85, No. 11, pp. 3005-3020.
Bhagwatwar et al, "Formulation And Stability Of Busulfan For Intravenous Administration In High-Dose Chemotherapy", Cancer Chemother Pharmacol, 1996, vol. 37, pp. 401-408.
Canellos, George, "Chronic Leulemias", In: Cancer: Principles and Practice of Oncology, $2^{nd}$ Ed. 1985, DeVita Jr et al (Eds.), J.B. Lippincott Co., Philadelphia, PA, pp. 1739-1752.
Carreras, Enric, "Veno-Occulsive Disease Of The Liver After Hemppoietic Cell Transplantation", Eur. J. Haematol., 2000, vol. 64, pp. 281-291.
Chattergoon et al, "An Improved Limited Sampling Method For Individualized Busulphan Dosing In Bone Marrow Transplantation In Children", Bone Marrow Transplantation, 1997, vol. 20, pp. 347-354.
Chyka et al, "Utility Of Acetylcysteine In Treating Poisonings And Adverse Drug Reactions", Drug Safety, Feb. 2, 2000, vol. 2, pp. 123-148.
Crowe et al, "Preservation Of Freeze-Dried Liposomes By Trehalose", Archives of Biochemistry and Biophysics, Oct. 1985, vol. 242, No. 1, pp. 240-247.
Czerwinski, et al, "Busulfan Conjugation By Glutathione S-Transferases α, μ, and π", Drug Metabolism and Disposition, 1996, vol. 24, No. 9, pp. 1015-1019.
De Leve, Laurie and Xiangdong Wang, "Role Of Oxidative Stress And Glutathione In Busulfan Toxicity In Cultured Murine Hepatocytes", PHARMACOLOGY, 2000, vol. 60, pp. 143-154.
Dix et al, "Association Of Busulfan Area Under The Curve With Veno-Occlusive Disease Following BMT", Bone Marrow Transplantation, 1996, vol. 17, pp. 225-230.
Ehninger et al, "Use Of Water -Soluble Busulfan Formulation-Pharmacokinetic Studies In A Canine Model", BLOOD, 1995, vol. 85, No. 11, pp. 3247-3249.

(Continued)

*Primary Examiner*—Michael G. Hartley
*Assistant Examiner*—Jake M. Vu
(74) *Attorney, Agent, or Firm*—Browdy & Neimark

(57) ABSTRACT

Pharmaceutically acceptable liposome-encapsulated busulphan formulations for parenteral administration are provided, as well as such formulations furthermore comprising glutathione and/or at least one glutathione precursor and a process for manufacture of the preparations. The formulations are stable, have improved biodistribution and significantly reduced side effects over those produced by oral administration or parenteral administration of free drug. The formulations are useful as part of stem cell and/or bone marrow transplant conditioning regimens. A method of treatment of a mammal by use of such formulations.

20 Claims, 13 Drawing Sheets

OTHER PUBLICATIONS

Gibbs et al, "Busulfan-Glutathione Conjugation Catalyzed by Human Liver Cytosolic Glutathione S-Transferases", Cancer Research, Aug. 15, 1996, vol. 56, pp. 3678-3681.

Glucksberg et al, "Clinical Manifestations of Graft-Versus-Host Disease in Human Recipients of Marrow from HL-A-Matched Sibling Donors", TRANSPLANTATION, 1974, vol. 18, No. 4, pp. 295-304.

Griffith, Owen and Alton Meister, "Potent and Specific Inhibition of Glutathione Synthesis bu Buthionine Sulfoximine (S-n-Butyl Homocysteine Sulfoximine)", The Journal of Biological Chemistry, Aug. 1979, vol. 254, No. 16, pp. 7558-7560.

Grochow et al, "Pharmacokinetics Of Busulfan: Correlation With Veno-Occulsive Disease In Patients Undergoing Bone Marrow Transplantation", Cancer Chemother Pharmacol, 1989, vol. 25, pp. 55-61.

Hare et al, "Characterization Of The Mechanisms Of Busulfan Resistance In A Human Glioblastoma Multiforme Xenograft", Cancer Chemother Pharmacol, 1997, vol. 40, pp. 409-414.

Hassan et al, "Busulfan Kinetics And Limited Sampling Model In Children With Leukemia And Inherited Disorders", Bone Marrow Transplantation, 1996, vol. 18, pp. 843-850.

Hassan et al, "Cerebrospinal Fluid And Plasma Concentrations Of Busulfan During High-Dose Therapy", Bone Marrow Transplantation, 1989, vol. 4, pp. 113-114.

Hassan, Moustapha and Hans Ehrsson, "Degradation Of Busulfan In Aqueous Solution", Journal of Pharmaceutical & Biomedical Analysis, 1986, vol. 4, No. 1, pp. 95-101.

Hassan, Moustapha and Hans Ehrsson, "Gas Chromatographic Determination Of Busulfan In Plasma With Electron-Capture Detection", Journal of Chromatography, 1983, vol. 277, pp. 374-380.

Hassan et al, "In Vivo Distribution of [$^{11}$C]-busulfan in *cynomolgus monkey* and in the Brain of a Human Patient", Cancer Chemother Pharmacol, 1992, vol, 30, pp. 81-85.

Hassan et al, "Pharmacokinetic And Metabolic Studies Of Busulfan In Rat Plasma And Brain", Eurpoean Journal of Drug Metabolism and Pharmacokinetics, 1988, vol. 13, No. 4, pp. 301-305.

Hassan, Moustapha and Hans Ehrsson, "Metabolism of $^{14}$C-busulfan In Isolated Perfused Rat Liver", European Journal of Drug Metabolism and Pharmacokinetics, 1987, vol. 12, No. 1, pp. 71-76.

Hassan et al, "The Pharmacodynamic Effect Of Busulfan In The P39 Myeloid Cell Line In Vitro", LEUKEMIA, 2001, vol. 15, pp. 1240-1247.

Kennedy, Gerald and Henry Sherman, "Acute and Subchronic Toxicity of Dimethylformamide and Dimethylacetamide Following Various Routes of Administration", Drug and Chemical Toxicology, 1986, vol. 9, No. 2, pp. 147-170.

Kinney et al, "Inhalation Studies In Rats Exposed To Dimethylacetamide (DMAc) From 3 to 12 Hours Per Day", Drug and Chemical Toxicology, 1993, vol. 16, No. 2, pp. 175-194.

Lerza et al, "Failure Of N-Acetylcysteine To Protect Against Cis-Dichlorodiammine-Platinum(II)-Induced Hematopoietic Toxicity In Mice", Life Sciences, 1986, vol. 38, pp. 1795-1800.

Ljungman et al, "High Busulfan Concentrations Are Associated With Increased Transplantation Related Mortality In Allogenic Bone Marrow Transplant Patients", Bone Marrow Transplantation, 1997, vol. 20, pp. 909-913.

Lowry et al, "protein measurement with the folin phenol reagent", J Biol Chem, 1951, vol. 193, pp. 265-275.

Lu et al, "Preliminary Results Of High-Dose Busulfan And Cyclophosphamide With Synergeneic Of Autologous Bone Marrow Rescue", Cancer Treatment Reports, 1984, vol. 86, No. 5, pp. 711-717.

Malley et al, "Chronic Toxicity/Oncogenicity Of Dimethylacetamide In Rats And Mice Following Inhalation Exposure", Fundamental and Applied Toxicology, 1995, vol. 26, pp. 80-93.

Marchand et al, "Biliary Excretion Of A Glutathione Conjugate Of Busulfan And 1,4-Diiodobutane In The Rat", Drug Metabolism and Disposition, 1988, vol. 16, No. 1, pp. 85-92.

Martino et al, "Fractionated Infusions Of Cryopreserved Stem Cells May Prevent DMSO-Induced Major Cardiac Complications In Graft Recipients", HAEMATOLOGICA, 1996, vol. 81, pp. 59-61.

Massa et al, "The Effect Of N-Acetylcysteine On Toxicity Of Cyclophosphamide And Doxorbubicin On Murine Hemopoietic Progenitors", Life Sciences, 1985, vol. 36, pp. 1141-1147.

Meister, Alton, "Glutathione Metabolism And Its Selective Modification", The Journal of Biological Chemistry, Nov. 1988, vol. 263, No. 33, pp. 17205-17208.

Mills et al, "Does The Breakpoint Within The Major Breakpoint Cluster Region (M-bcr) Influence The Duration Of The Chronic Phase In Chronic Myeloid Meukemia? An Analytical Comparison Of Current Literature", The Journal of the American Society of Hematology, Sep. 1991, vol. 78, No. 5, pp. 1155-1161.

Mulder, Gerard and Sivi Ouwerkerk-Mahadevan, "Modulation Of Glutathione Conjugation In Vivo: How To Decrease Glutathione Conjugation In Vivo Or In Intact Cellular Systems In Vitro", Chemico-Biological Interactions, 1997, vol. 105, pp. 17-34.

Oakhill et al, "Busulfan Lung In Childhood", J Clin Pathol, 1981, vol. 34, pp. 495-500.

Papahadjopoulos, Demetrios and N. Miller, "Phospholipid Model Membranes: I. Structural Characteristics of Hydrated Liquid Crystals", Biochimica et Biophysica Acta, 1967, vol. 135, pp. 624-638.

Pawlowska et al, "Relationship Of Plasma Pharmacokinetics Of High-Dose Oral Busulfan To The Outcome Of Allogeneic Bone Marrow Transplantation In Children With Thalassemia", Bone Marrow Transplantation, 1997, vol. 20, pp. 915-920.

Ringden, et al, "Increased Risk Of Chronic Graft-Versus-Host Disease, Obstructive Bronchiolitis, And Alopecia With Busulfan Versus Totla Body Irradiation: Long-Term Results Of A Randomized Trial In Allogeneic Marrow Recipients With Leukemia", BLOOD, 1999, vol. 93, No. 7, pp. 2196-2201.

Ringden et al, "N-acetylcysteine for Hepatic Veno-Occlusive Disease After Allogeneic Stem Cell Transplantation", Bone Marrow Transplantation, 2000, vol. 25, pp. 993-996.

Ringden et al, "A Randomized Trial Comparing Busulfan With Total Body Irradiation As Conditioning In Allogeneic Marrow Transplantation Recipients With Leukemia: A Report From The Nordic Bone Marrow Transplantation Group", BLOOD, 1994, vol. 83, No. 9, pp. 2723-2730.

Ritter et al, "Determination Of Tetradrothiophene Formation As A Probe Of In Vitro Busulfan Metabolism By Human Glutathione S-Transferase A1-1: Use Of A Highly Sensitive Gas Chromatographic-Mass Spectrometric Method", Journal of Chromatography B, 1999, vol. 730, pp. 25-31.

Rudolph, Alan, "The Freeze-Dries Preservation of Liposome Encapsulated Hemoglobin: A Potential Blood Substitute", CRYOBIOLOGY, 1988, vol. 25, pp. 277-284.

Santos et al, "Marrow Transplantation For Acute Nonlymphocytic Leukemia After Treatment With Busulfan And Cyclophosphamide", The New England Journal of Medicine, 1983, vol. 309, No. 22, pp. 1347-1353.

Schuler et al,. "Busulfan Pharmacokinetics In Bone Marrow Transplant Patients: Is Rug Monitoring Warranted?", Bone Marrow Transplantation, 1994, vol. 14, pp. 759-765.

Schuler et al, "Intravenous Busulfan Conditioning", Bone Marrow Transplantation, Mar. 1998, vol. 21, Supple. 1, abstract 351.

Selig et al, "Radioprotective Effect Of N-Acetylcysteine On Granulocyte/Macrophage Colony-Forming Cells Og Human Bone Marrow", J Cancer Res Clin Oncol, 1993, vol. 119, pp. 346-349.

Shulman, H.M. and W. Hinterberger, "Hepatic Veno-Occulsive Disease—Liver Toxicity Syndrome After Bone Marrow Transplantation", Bone Marrow Transplantation, 1992, vol. 10, pp. 197-214.

Slattery et al, "Graft-Rejection And Toxicity Following Bone Marrow Transplantation In Relation To Busulfan Pharmacokinetics", Bone Marrow Transplantation, 1995, vol. 16, pp. 31-42.

Sperling, Steffen and Inger Larsen, "Toxicity Of Dimethylsulfoxide (DMSO) To Human Corneal Endothelium In Vitro", Acta Opthalmologica, 1979, vol. 57, pp. 891-898.

Tietze, Frank, "Enzymic Method For Quantitative Determination Of Nanogram Amounts Of Total And Oxidized Glutathione", Analytical Biochemistry, 1969, vol. 27, pp. 502-522.

Vassal et al, "Dose-Dependent Neurotoxicity Of High-Dose Busulfan In Children: A Clinical And Pharmacological Study", Cancer Research, 1990, vol. 50, pp. 6203-6207.

Vassal et al, "Is 600 mg/m$^2$ the Appropriate Dosage of Busulfan in Children Undergoing Bone Marrow Transplantation", BLOOD, 1992, vol. 79, No. 9, pp. 2475-2479.

Weiner et al, "Liposomes As A Drug Delivery System", Drug Development and Industrial Pharmacy, 1989, vol. 15, No. 10, pp. 1523-1554.

Yellowless et al, Dimethylsulphoxide-Induced Toxicity, The Lancet, Nov. 1980, vol. 2, pp. 10041006.

* cited by examiner

PHARMACEUTICAL COMPOSITION, A METHOD OF PREPARING IT AND A METHOD OF TREATMENT BY USE THEREOF

The present application is a continuation-in-part of application Ser. No. 09/719,840, filed Apr. 6, 2001 now abandoned, which was a 371 of PCT of PCT/SE99/01093, filed Jun. 17, 1999, and claims priority from U.S. provisional applications No. 60/376,533, filed May 1, 2002, and No. 60/089,759, filed Jun. 18, 1998, all of which are hereby incorporated by reference herein.

FIELD OF THE INVENTION

This invention relates to the fields of biochemistry and medicine, and in particular to a pharmaceutical composition of busulphan having enhanced therapeutic efficiency coupled to decreased negative side effects and to a method of therapeutic treatment of a mammal by use of such composition.

BACKGROUND OF THE INVENTION

Busulphan (1,4-bis-(methanesulphonyloxy)butan) is a bifunctional alkylating agent with potent antitumor effects. It has been widely used for treatment of malignant diseases, especially hematological malignancies and myeloproliferative disorders. Its use was for a long time restricted to low dose oral therapy, with recorded side effects such as busulphan-induced pulmonary fibrosis (Oakhill et al. 1981. J. Clin. Pathol. 34(5):495-500.) and irreversible myelo-suppression (Canellos 1985. Chronic Leukemias In: Cancer: Principles and Practice of Oncology, pp 1739-1752). In 1983, high-dose combination chemotherapy based on oral busulphan for pretransplant-conditioning of patients undergoing both autologous and allogeneic bone marrow transplantation (Santos, G. W. et al. 1983. N. Engl. J. Med. 309: 1347-1353; Lu, C. et al. 1984. Cancer Treatm. Repts. 68: 711-717) was introduced. Since then, high dose busulphan replaces total body irradiation (TBI), most commonly in combination with cyclophosphamide, and has proven to be a most effective anti-leukemic regimen when used in conjunction with autologous or allogeneic hematopoietic stem cell support. The main advantage of high-dose busulphan therapy for use in marrow ablation treatment is that total body irradiation regimen is avoided, which is especially advantageous for young children and adults who received TBI as part of their initial therapy.

Oral busulphan in combination with cyclophosamide has several serious side effects. Reported side effects are fatal liver failure (Miller, C. et al. 1991. Blood 78: 1155), neurological disturbances like grand mal seizures, venoocclusive disease, severe nausea and vomiting (Vassal, G. et al. 1990. Cancer Res. 50: 6203-6207) as well as side effects in the lungs, such as interstitial pneumonia (Bandini, G. et al. 1994. Bone Marrow Transpl. 13: 577-581).

Therefore attempts have been made to improve the clinical utility of the busulphan drug by providing a busulphan formulation for parenteral administration. U.S. Pat. Nos. 5,430,057 and 5,559,148 disclose physiologically acceptable solutions of busulphan, wherein N',N-dimethyl-acetamide, polyethylene glycol, propylene glycol, glycerin cyclodextrin, hydroxypropylbetacyclodextrin are used as solvents. In two other studies busulphan was dissolved in dimethylacetamide (DMA) (Bhagwatwar H. P, Phadungpojna S, Chow D. S., Andersson B. S. 1996. Cancer Chemother Pharmacol 37: 401) and dimethylsulfoxide (DMSO) (Ehninger G, Schuler U, Renner U, Ehrsam M, Zeller K. P, Blanz J, Storb R, Deeg H. J. 1995. Blood 85: 3247). However, despite the very promising results, these organic solvents have their own toxicity (Kennedy Jr G. L, Sherman H. 1986. Drug and Chemical Toxicology 9: 147; Kinney L. A, Burgess B. A, Stula E. F, Kennedy Jr G. L. 1993. Drug and Chemical Toxicology 16: 175; Malley L. A, Slone Jr T. W, Makovec G. T, Elliott G. S, Kennedy Jr G. L. 1995. Fundam Appl Toxicol 28: 80; Martino M, Morabito F, Messina G, Irrera G, Pucci G, Iacopino P. 1996. Haematologica 81: 59; Sperling S, Larsen I. G. 1979. Acta Opthalmol (Copenh) 57: 891; Yellowlees P, Greenfield C, McIntyre N. 1980. Lancet 2: 1004). Further, it seems as if DMSO activates the metabolism of busulphan in the liver, resulting in reduced concentrations of busulphan in the blood of the patient after a few days regimen (Shuler et al. 1997. Abstract EBMT-meeting, Chamonix, France). The Spartaject™ technology has tried to achieve a formulation of busulphan for parenteral administration by forming microcrystals of busulphan coated with lecithin (or other phospholipid) dissolved in mannitol and water. The size of these microcrystals is 0.1 μm. The main problem with this formulation is precipitation of the microcrystals during infusion of the drug. Also nothing is known about their biodistribution. Both busulphan dissolved in organic solvents and oral busulphan cross the blood brain barrier, giving rise to central nerve system toxicity.

Several studies have shown a correlation between exposure to busulphan and transplantation related liver toxicity, such as venoocclusive disease (VOD) in patients undergoing SCT (Ringdén O, Ruutu T, Remberger M, et al. A randomised trial comparing busulfan with total body irradiation as conditioning in allogeneic marrow transplant recipients with leukemia: A report from the Nordic Bone Marrow Transplant Group. Blood 1994; 83: 2723-2730; Grochow L B, Jones R J, Brundrett R B, Braine H G, Chen T L, Saral R, et al. Pharmacokinetics of busulfan: correlation with venoocclusive disease in patients undergoing bone marrow transplantation. Cancer Chemother Pharmacol 1989; 25(1): 55-61; Bearman S I. The syndrome of hepatic venoocclusive disease after marrow transplantation. Blood 1995; 85: 3005; Shulman H M, Hinterberger W. Hepatic venoocclusive disease—liver toxicity syndrome after bone marrow transplantation. Transplantation 1992; 10: 197.). Apart from acute GVHD and infections, VOD is one of the common early complications with a potential fatal outcome following SCT. Hepatic VOD is a clinical syndrome consisting of jaundice, ascites and/or unexplained weight gain, and hepatomegaly and/or upper quadrant abdominal pain. It is a life-threatening complication and the reported incidences vary considerably; though it may improve spontaneously, the mortality of severe VOD is about 20-50%.

Another problem of the prior art methods for treatment with busulphan as a part of the myeloablative regimen prior to stem cell transplantation is that the dosage has been difficult to optimize due to the wide inter-patient variability in pharmacokinetics in combination with the narrow therapeutic window of busulphan. A suboptimal dosage of busulphan expressed as low AUC after oral administration was correlated to a minimal toxicity in children and both graft rejection and relapse in adults (Slattery J T, Sanders J E, Buckner C D, et al: Graft-rejection and toxicity following bone marrow transplantation in relation to busulfan pharmacokinetics [published erratum appears in Bone Marrow Transplant 1996 October; 18(4):829]. Bone Marrow Transplant 16: 31-42, 1995; Pawlowska A B, Blazar B R, Angelucci E, et al: Relationship of plasma pharmacokinetics of high-dose oral busulfan to the outcome of allogeneic bone marrow transplantation in children with thalassemia. Bone Marrow Transplant 20: 915-20, 1997). On the other hand, as mentioned herein above, high exposure to busuphan during conditioning has been correlated to VO and also interstitial pneumonia and CNS toxicity (Vassal G, Deroussent A, Hartmann O, et al: Dose-dependent neurotoxicity of high-dose busulfan in children: a clinical and pharmacological study. Cancer Res 50: 6203-7, 1990; Grochow L B, Jones R J, Brundrett R B, et al: Pharmacokinetics of busulfan: correlation with veno-occlusive disease in patients undergoing bone marrow transplantation. Cancer Chemother Pharmacol 25: 55-61, 1989; Dix S P, Wingard J R, Mullins R E, et al: Association of busulfan area under the curve with veno-occlusive disease following BMT. Bone Marrow Transplant 17: 225-30, 1996). High plasma concentrations of busulphan were also correlated to transplantation related mortality occurring before day 100 post transplantation (Ljungman P, Hassan M, Bekassy A N, et al: High busulfan concentrations are associated with increased transplant-related mortality in allogeneic bone marrow transplant patients. Bone Marrow Transplant 20: 909-13, 1997). In a randomized study, busulphan compared to total body irradiation has been found to be associated with an increased risk of hemorrhagic cystitis, VOD, obstructive bronchiolitis, alopecia and chronic GVHD (Ringden O, Remberger M, Ruutu T, et al: Increased risk of chronic graft-versus-host disease, obstructive bronchiolitis, and alopecia with busulfan versus total body irradiation: long-term results of a randomized trial in allogeneic marrow recipients with leukemia. Nordic Bone Marrow Transplantation Group. Blood 93: 2196-201, 1999).

To optimize treatment with oral busulphan and to minimize its toxicity during high dose therapy, many investigators have suggested therapeutic monitoring using limited sampling models followed by dose adjustment (Vassal G, Deroussent A, Challine D, et al: Is 600 mg/m2 the appropriate dosage of busulfan in children undergoing bone marrow transplantation? Blood 79: 2475-9, 1992; Hassan M, Fasth A, Gerritsen B, et al: Busulphan kinetics and limited sampling model in children with leukemia and inherited disorders. Bone Marrow Transplant 18: 843-50, 1996; Chattergoon D S, Saunders E F, Klein J, et al: An improved limited sampling method for individualised busulphan dosing in bone marrow transplantation in children. Bone Marrow Transplant 20: 347-54, 1997; Schuler U, Schroer S, Kuhnle A, et al: Busulfan pharmacokinetics in bone marrow transplant patients: is drug monitoring warranted? Bone Marrow Transplant 14: 759-65, 1994). However, the usefulness of this strategy is limited due to the restricted possibility to perform sample analysis, the losses of the drug through emesis and/or the irregular and slow absorption reported in some patients.

From the above, it appears that treatment of a mammalian patient with busulphan suffers from serious drawbacks due to the chemical nature of the busulphan molecule that makes its administration and proper dosage problematic, as well as to the inherent toxicity of the molecule, resulting in secondary effects that may lead to life-threatening conditions.

The tripeptide glutathione (g-glutamylcysteinylglycine, GSH) is an important component of the intracellular defense against toxic challenge. It is a sulfhydryl (—SH) antioxidant, an antitoxin, and enzyme cofactor, ubiquitous in animals, plants, and microorganisms, often attaining millimolar levels inside cells.

It is believed that low constitutive levels of GSH in centrilobular hepatocytes, together with further GSH exhaustion by cytotoxic drugs or radiation contributes to development of VOD (Carreras E. Venoocclusive disease of the liver after hematopoietic cell transplantation. Eur J Haematol 2000; 64(5): 281-91). Involvement of GSH in the metabolism of busulphan has been studied in animal models and in man (Marchand D H, Remmel R P, Abdel-Monem M M. Biliary excretion of a glutathione conjugate of busulfan and 1,4 diiodobutane in the rat. Drug Metab Dispos 1988; 16(1): 85-92; Hassan M, Ehrsson H. Metabolism of 14C-busulfan in isolated perfused rat liver. Eur J Drug Metab Pharmacokinet 1987; 12(1):71-6; Ritter C A, Bohnenstengel F, Hofmann Um Kroemer H K, Sperker B. Determination of tetrahydrothiophene formation as a probe of in vitro busulfan metabolism by human glutathione S-transferase A1-1: use of a highly sensitive gas chromatographic-mass spectrometric method. J Chromatogr B Biomed Sci Appl 1999; 730(1):25-31). Several investigations have conformed that busulphan is metabolized in the liver through conjugation with GSH catalyzed by glutathione S-transferase (GST). The reaction is catalyzed in human liver mainly by GST-A1-1 (Czerwinski M, Gibbs J P, Slattery J T. Busulfan conjugation by glutathione S-transferase alpha, my and pi. Drug Metab Dispos 1996; 24(9): 1015-9; Gibbs J P, Czerwinski M, Slattery J T. Busulfan-glutathione conjugation catalyzed by human liver cytosolic glutathione S-transferases. Cancer Res 1996; 56(16):3678-81). Treatment with busulphan depleted GSH by 60% in murine hepatocytes in vivo and by 50% in vitro (De Leve L D, Wang X. Role of oxidative stress and glutathione in busulfan toxicity in cultured murine hepatocytes. Pharmacology 200; 60(3):143-54). In the same study, modulation of the cellular levels of GSH changed hepatocyte cytotoxity of busulphan: cells depleted of GSH were more sensitive and cells with increased GSH less sensitive to the toxic effect. Precursors of GSH, such as N-acetyl-L-cysteine (NAC) or methionine, increase cellular content of GSH (Meister A. Glutathione metabolism and its selective modification. J Biol Chem 1988; 263(33):17205-8).

The GSH precursor NAC is used to treat hepatotoxicity induced by acetaminophen (Chyka, P. A., Butler, A. Y., Holliman, B. J., and Herman, M. I. Utility of acetylcysteine in treating poisonings and adverse drug reactions. Drug Saf, 22: 123-148, 2000.). NAC has few and mild side effects. Recently, a case report on three patients with VOD, who were successfully treated with NAC, was published (Ringden, O., Remberger, M., Lehmann, S., Hentschke, P., Mattsson, J., Klaesson, S., Aschan, J.: N-acetylcysteine for hepatic veno-occlusive disease after allogeneic stem cell transplantation. Bone Marrow Transplant. 25: 993-996, 2000).

On the other hand, depletion of GSH increases toxicity of alkylating agents in most cell systems studied. GSH may be depleted in vivo by treatment with buthionine sulfoximine and in vitro by incubation in medium without sulphur amino acids, or by treatment with buthionine sulfoximine or ethacrynic acid (Mulder, G. J. and Ouwerkerk-Mahadevan, S. Modulation of glutathione conjugation in vivo: how to decrease glutathione conjugation in vivo or in intact cellular systems in vitro. Chem Biol Interact, 105: 17-34, 1997.). L-buthionine-[S,R]-sulfoximine (BSO) is an irreversible inhibitor of γ-glutamylcysteine synthetase, an enzyme catalyzing the first step of de novo synthesis of GSH in cells (Griffith, O. W. and Meister, A. Potent and specific inhibition of glutathione synthesis by buthionine sulfoximine (S-n-butyl homocysteine sulfoximine). J Biol Chem, 254: 7558-7560., 1979.).

Prior to the present invention, the effect of modulation of GSH on busulphan-induced cytotoxicity had not been studied in hematopoietic cells. Though hematopoietic stem cells do not express GSTA1, they do express other GST isoforms. In analogy with the cytoprotective effect obtained by administration of a GSH precursor to hepatocytes, a reasonable hypothesis would be that such administration would also help protecting target cells, such as hematopoietic cells during a myealoablative treatment, against the cytotoxic effects of an alkylating agent such as busulphan, thereby reducing the treatment efficiency. This would seem to rule out use of GSH or a GSH precursor during busulphan treatment.

A liposome is a completely closed lipid bilayer membrane which defines a closed aqueous compartment. Liposomes are microscopic delivery vesicles made, in part, from phospholipids which form closed, fluid filled spheres when mixed with water. Phospholipid molecules are polar, having a hydrophilic ionizable head, and a hydrophobic tail consisting of long fatty acid chains. Thus when sufficient phospholipid molecules are present with water, the tails spontaneously associate to exclude water while the hydrophilic phosphate heads interact with water. Liposomes may be either unilamellar, comprised of one lipid bilayer membrane, or bilayer liposomes, comprised of two layers of lipids. In the latter liposomes the outer layer of lipid molecules are oriented with their hydrophilic head portions towards the external aqueous medium and their hydrophobic tails pointed inwards towards the interior of the liposome. The inner layer of lipids lies directly beneath the outer layer; the lipids are oriented with their heads facing the aqueous interior of the liposome and their tails towards the tails of the outer lipid layer. Multilamellar liposomes are composed of more than one lipid bilayer membrane, which define more than one closed compartment and are concentrically arranged.

Since the chemical composition of many drugs precludes their intravenous administration, liposomes can be very useful in adapting these drugs for intravenous delivery. Many hydrofobic drugs fall into this category because they cannot be easily dissolved in a water-based medium and must be dissolved in alcohols or surfactants which have been shown to cause toxic reactions in vivo. Liposomes, composed of predominantly lipids, with or without cholesterol, are nontoxic. Further, liposomes have the potential of providing a controlled release of the administered drug over an extended period of time, and of reducing toxic side effects of the drug, by limiting the concentration of the free drug in the bloodstream. Liposomes can also alter the tissue distribution and uptake of drugs, and the altered tissue distribution can significantly increase the therapeutic effectiveness of the drug. Liposome/drug compositions can for these reasons increase the convenience of therapy by allowing higher drug dosage and less frequent drug administration.

The original liposome preparation of Bangham et al. (J. Mol. Biol., 1965, 13238-252) involves suspending phospholipids in an organic solvent which is then evaporated to dryness leaving a phospholipid film or powder. Next, hydration is performed, i.e. an aqueous phase is added to the phospholipid film and the mixture is dispersed by mechanical means resulting in liposomes consisting of multilamellar vesicles (MLVs). This preparation provides the basis for the development of small sonicated unilamellar vesicles (SUVs) described by Papahadjopoulos et al. (Biochim. Biophys. Acta. 1967, 135: 624-638), and large unilamellar vesicles (LUVs).

A variety of sterols and their water soluble derivatives such as cholesterol hemisuccinate as well as a variety of tocopherols and their water soluble derivatives have been used to form liposomes. Liposomes themselves have been reported to have no significant toxicities in previous human clinical trials where they have been given intravenously.

Prior to the present invention, busulphan had been therapeutically used for a very long time and at the priority date of the application the toxicity of busulphan was well-known. However, in spite of the serious and well-documented side-effects of busulphan therapy and in spite of the knowledge that the toxicity might be reduced by liposomal encapsulation of busulphan, prior to the application this had not been practically done and there existed no practical method permitting to do this.

In the literature (Weiner et al: Lipsomes as a Drug Deliver System, Drug Development and Industrial Pharmacy, 15(10), 1523-1554), it has been pointed out that "the maximum amount of drug that can be entrapped within a liposome is dependent on its total solubility in each phase". Busulphan has very limited solubility in both polar and non-polar solvents. Though described as a lipophilic compound, it in fact is poorly soluble in oils, carbon tetrachloride or any other very lipophilic solvent. Busulphan also is only very slightly water soluble (less than 1 microgram/ml at 25° C.). Therefore, prior to the present invention there existed no way of preparing a liposomal composition having therapeutically useful content of busulphan enclosed in liposomes.

SUMMARY OF THE INVENTION

As stated herein above, this invention provides, for the first time, a liposome-encapsulated busulphan. The formulations give water-soluble, highly stable, pharmacologically active busulphan. Liposome-encapsulated busulphan overcomes the insolubility problem of the busulphan drug when administered intravenously. The main advantage of liposome-encapsulated busulphan is that the tissue distribution of the drug to the bone marrow and spleen is increased. Since these are the target organs for the therapy, this results in increased therapeutic effectiveness and reduced toxic side effects of the drug. Further there is no accumulation of the drug in the liver or other organs known to be susceptible for busulphan toxicity. Liposome encapsulated busulphan according to the invention has with good result been administered to humans (see Examples 8 and 9).

One first object therefore is to provide a liposome composition comprising busulphan encapsulated in a plurality of liposomes (i.e. liposomal busulphan).

A further object of the invention is to provide a pharmaceutical composition comprising busulphan, having a substantially enhanced therapeutic efficiency in conjunction with substantially reduced negative side effects.

Yet another object of the invention is to provide a method of therapeutic treatment by use of a composition comprising busulphan, such method having a substantially enhanced efficiency while at the same time having substantially reduced negative side effects.

One particularly preferred aspect of the present invention is based upon the discovery that, contrary to what might be expected, modulation of GSH content in haematopoietic cells does not counteract the hematotoxic effect of busulphan, making it possible to reduce the unwanted negative side effects of busulphan therapy while at the same time preserving the wanted hematotoxic effects thereof.

Consequently, according to a particularly preferred embodiment of the invention, said pharmaceutical composition comprising liposomal busulphan also comprises GSH and/or at least one biochemical precursor of GSH. The GSH or precursor of GSH may be present either within the liposomes, or in the surrounding medium thereof, or both.

According to a particularly preferred embodiment of the invention, such method also comprises the administration of a pharmaceutical composition comprising GSH and/or at least one biochemical precursor of GSH.

According to a further aspect the invention provides a method of preventing pathological conditions caused by cellular depletion of GSH in relation to treatment with busulphan.

According to one particular aspect the invention provides a method of preventing pathological conditions such as veno-occlusive disease, interstitial pneumonia and neurotoxicity (seizures) in relation to treatment with busulphan.

According to an advantageous embodiment of the invention, said compositions and methods are used in high dose busulphan treatment, such as in myeloablative or non-myeloablative conditioning regimens in view of e.g. stem cell transplantations.

Further aspects and embodiments of the invention are as defined in the claims.

DETAILED DESCRIPTION OF THE INVENTION

Figure 1:
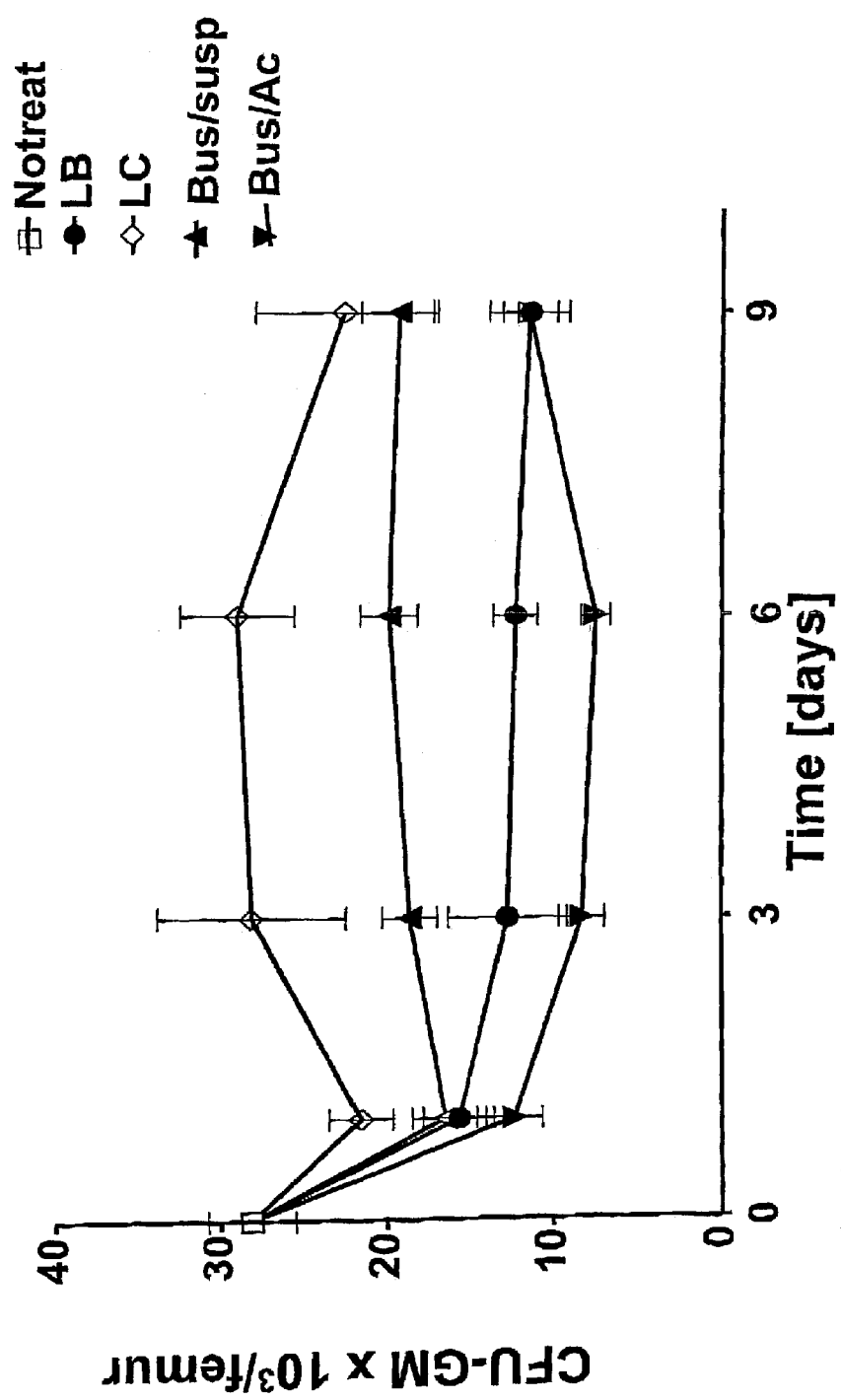
FIG. 1. Myelosuppression kinetics of intravenously administered liposomal busulphan and orally administered busulphan after bone marrow transplantation conditioning regimen. Each data point represents the mean ±SD for 3 to 7 animals. All statistical calculations were made using median values.

The present invention provides water soluble, highly stable, pharmacologically active busulphan by stabilizing the busulphan drug in liposomes. The liposomes are comprised of (i.e. their membranes comprise) lipids such as phosphatidylcholine, phosphatidylserine, symmetric or asymmetric 1,2-Dioleoyl-sn-glycero-3-phosphate, cholesterol, cardiolipin, stearylamine, dicetylphosphate and phosphatidylglycerol. The liposomes may additionally comprise alpha-tocopherol.

In a preferred embodiment the liposomes comprise L-a-phosphatidylcholine, 1,2-dioleoyl-sn-glycero-3-phosphate and cholesterol in a molar ratio of about 10:1:10. In other preferred embodiments the liposomes comprise phosphatidylserine, phosphatidylcholine and cholesterol in a molar ratio of about 3:7:10, or cardiolipin, phosphatidylcholine and cholesterol in a molar ratio of about 1:4:1.5, or phosphatidylcholine, cholesterol and stearylamine in a molar ratio of about 7:1:1. In all four of these compositions, the content of each lipid may vary within approximately 30%.

During preparation of the liposomes organic solvents may be used to dissolve the lipids. Suitable solvents include, but are not limited to, chloroform, methanol, dimethylsulphoxide (DMSO), methylene chloride, ether, acetone and solvent mixtures such as benzene-methanol. In a preferred embodiment chloroform is used. Busulphan is added at this stage and the mixture is dried by evaporation, or other means, to a thin film.

The mixture can then be hydrated with e.g. aqueous glucose, sodium chloride, dextran, mannitol, ringer acetate, or sodium bicarbonate. The pH of the internal environment of the liposomes may be reduced to pH 2-6, which prevents hydrolysis. Phosphate, acetate, or citrate buffers may be used to adjust pH.

The liposome suspension may be annealed for 20-30 minutes at −60 to −80° C. Several methods may be used to form the liposomes of the invention, e.g. by vortexing or shaking. Multilamellar vesicles (MLVs) (0.05-5 µm), stable plurilamellar vesicles (SPLVs) or reverse phase evaporation vesicles (REVs) may be used. Preferably, MLVs are extruded through filters forming LUVs of sizes depending on the filter pore size. Polycarbonate filters of 50 to 300 nm pore sizes can be used. The liposomes are small unilamellar vesicles (SUV), rather than multilamellar vesicles (MLV). However, both SUVs and MLVs are within the scope of the invention. The liposomes are about 50-300 nm in size.

The busulphan-containing liposomes according the invention contain about 10 to 75 mg of lipid/mL. They have a drug (busulphan) to lipid molar ratio of about 1:2-1:140. Once the liposomes have been hydrated, they can be stored at 4° C. for 20 days (see Example 1). To prolong the shelf life the liposomes can be dehydrated, e.g. freeze-dried. When the dehydrated liposomes are to be used, rehydration is accomplished by adding an aqueous solution, e.g. distilled water or an appropriate buffer, to the liposomes and allowing them to rehydrate.

Procedures for freeze-drying liposomal compositions are well-known to the skilled person, and described in the literature (e.g. Crowe L M, Crowe J H, Rudolph A, Womersley C, Appel L: Preservation of freeze-dried liposomes by trehalose. Arch Biochem Biophys 1985 October; 242(1): 240-7; Rudolph A S: The freeze-dried preservation of liposome encapsulated hemoglobin: a potential blood substitute. Cryobiology 1988 Aug., 25(4):277-84). In order not to unduly decompose busulphan, high-temperature procedures should be avoided.

The liposomes of the present invention can be administered alone but will generally be administered together with a pharmaceutically acceptable carrier. The preparations may be administered parenterally, most preferably intravenously.

Since dosage regimens for busulphan are well known, the amount of the liposomal busulphan which is effective of therapeutic for the treatment of the above mentioned diseases or conditions in humans will be apparent to those skilled in the art. However, the present invention provides a method of determining an optimum dosage of busulphan.

Consequently, by use of the inventive method of preparing liposomal busulphan, a pharmaceutical composition is provided having reduced negative side-effects, such as venoocclusive disease, and enhanced efficiency as compared to the busulphan compositions according to the prior art.

According to a particularly preferred aspect the present invention provides a means of further reducing the negative effects.

As pointed out herein above, veno-occlusive disease is a serious and potentially lethal condition, which may occur as a side effect of busulphan therapy. However, the present inventors have found that administration of GSH or precursors of GSH, such as: N-acetylcysteine (NAC), methionine, cysteine, glutamine, cystine, homocysteine, glycine, cysteinylglycine, glutamyl aminoacid, glutamyl cysteine, prior to and/or concurrently with and optionally after administration of high dose busulphan, is effective to protect from the occurrence of veno-occlusive disease as a side effect of high-dose busulphan treatment.

By precursor of GSH is meant a compound that through intracellular reactions within the body of a mammal is transformed into the former, i.e. a biological—or biochemical—precursor. GSH precursors are naturally occurring amino acids and dipeptides and as such are practically devoid of toxicity when given to a mammal. These compounds may be used as a single agent or in combination with each other.

Any of the above-listed GSH precursors may be applied according to the invention. However, the presently preferred GSH precursors for use according to the invention are NAC and methionine. GSH precursors such as listed herein above are generally commercially available, and may be purchased e.g. from NM Pharma, Tika, Sigma, Aldrich and Merck.

The GSH or its precursors may be given by intravenous, topical (intramuscular, subcutaneous, intraperitoneal or intra-tumoral) and oral administration. They preferably are administered prior to and/or in combination with and optionally after the high dose busulphan treatment.

In case the pharmaceutical composition comprising GSH and/or at least one precursor of GSH is prepared separately from the busulphan composition, and either administered separately from or at the same time as the latter, the formulation of the GSH precursor pharmaceutical composition, e.g. the selection of suitable excipients, will be known to the person skilled within the pharmaceutical field Optionally, further active ingredients may be administered in combination with the high dose busulphan/GSH precursor and or GSH, such as other cytostatics, e.g. cyclophosphamide, vepesid and melphalan.

The GSH and/or GSH precursor may be present in the pharmaceutical preparation coupled, e.g. through a covalent linkage, to a pharmaceutically acceptable lipid, e.g. phosphatidyl choline; 1,2-dioleolyl-sn-glycero-3-phosphate; phosphatidylserine; cardiolipin; dipalmitoyl-phosphatidylcholine; distearoylphosphatidylcholine; dioleoylphosphatidylethanolamine; diacetylphosphate; stearylamin; phosphatidylglycerol; dimyristoloxy-propyl-3-dimethylhydroxyethylammoniumbromide; and N-palmitoyl homocysteine. Such a lipid modified by addition of GSH and/or GSH precursor to its structure may be seen as a prodrug form of the GSH and/or GSH precursor.

In one embodiment of the invention, GSH and/or one or several GSH precursors is (are) administered in combination with busulphan, to a mammal in need of cytotoxic treatment, as a liposomal preparation wherein the GSH and/or GSH precursor(s) may be present in the surrounding medium and/or comprised within the same liposomes as busulphan and/or within separate liposomes.

The GSH or precursors of GSH, single or in combination, selected from e.g. N-acetylcysteine (NAC), methionine, cysteine, glutamine, cystine, homocysteine, glycine, cysteinylglycine, glutamyl aminoacid and glutamylcysteine, may be added during the preparation of liposomes or as a solution added as a solvent to lyophilized liposomal busulphan, whereby glucose solution, distilled water or NaCl solution, or other equivalent solution may be used to dissolve the preparation.

The GSH and/or GSH precursor may be administered at a daily dosage of e.g. from 0.5 mg/kg of body weight to 300 mg/kg of body weight or more during a period starting at the same time as, prior to or after, starting the busulphan administration and preferably extending through the entire period of treatment with busulphan and even beyond this period. As an example, treatment with the GSH precursor may start two weeks before the busulphan treatment period and continue until two weeks after termination of busulphan treatment. The GSH precursor dosage may be varied, e.g. a lower daily dosage before starting busulphan administration, followed by a higher daily dosage during the busulphan administration period, and a lower daily dosage for a period after the busulphan administration period. Also the dosage may be successively increased and/or reduced. Of course both the duration of treatment and the dosage are to be determined by the skilled practitioner in charge, taking account of such parameters as physical condition, size, age etc. of the treated patient.

Although the method of treating a mammal by administration of busulphan according to the invention is performed by use of a liposomal preparation thereof, it should be understood that the present invention also encompasses using GSH and/or the GSH precursor in combination with a non-liposomal busulphan composition.

The total daily dose of busulphan suitably ranges from 0.25 mg/kg-25 mg/kg of body weight or 200-750 mg/m2, more preferably 400-600 mg/m$^2$, most preferably 500 mg/m$^2$ of body surface, administered as a single dose or divided in multiple doses for several days. NAC, for example, suitably may be administered at 0.5 mg/kg-200 mg/kg of body weight as a single dose or as repeated doses.

During the busulphan treatment period, GSH and/or the GSH precursor(s) may be included in the same pharmaceutical preparation as the busulphan, preferably a liposomal preparation. However, GSH and/or the GSH precursor also may be administered as a conventional pharmaceutical preparation.

The invention will herein below be described in greater detail by reference to the following non-limiting examples.

EXAMPLES

Example 1

Preparation of Liposome-Encapsulated Busulphan Comprising L-α-Phosphatidylcholine, 1,2-dioleolyl-sn-glycero-3-phosphate and cholesterol Materials Busulphan (1,4-bis[methanesulphonyloxy]butane) was obtained from Sigma Chemicals, St Louis, USA.1,4-$^{14}$C-succinic acid) was purchased from Amersham, UK. Cholesterol, L-α-phosphatidylcholine (chicken egg, 100 mg/mL) and 1,2-dioleolyl-sn-glycero-3-phosphate (monosodium salt, 20 mg/mL) were obtained from Avanti Polar-Lipids Inc., Alabama USA. Aqueous glucose- and sodium chloride solutions (50 mg/mL and 9 mg/mL, respectively) were obtained from Pharmacia & Upjohn, Sweden.

Liposomal busulphan was prepared using L-α-Phosphatidylcholine, 1,2-dioleolyl-sn-glycero-3-phosphate and cholesterol. L-α-phosphatidylcholine (EPC), 1,2-dioleolyl-sn-glycero-3-phosphate (DOPA) and cholesterol in the molar ratio 9.45:1:9.4, were dissolved in chloroform. Busulphan was added. The mixture of lipids and busulphan was dried by evaporation to a thin film coating the inside of a round glass vessel. Any traces of solvent were removed under a gentle stream of nitrogen. The mixture was then hydrated with 25 mL of glucose solution (50 mg/mL, pH 4.0) or 25 mL of sodium chloride solution (9 mg/mL). Multilamellar vesicles were formed by vortexing the lipid-aqueous mixture for 10 minutes at room temperature. The suspension was transferred to an Extruder (LiposoFast 50, Avestin, Ottawa, Canada) and extruded under nitrogen, through 2 stacked polycarbonate filters of 100 nm pore size 5 times. All these steps were performed under aseptic conditions. Busulphan concentrations were determined before and after filtration to determine the entrapment efficiency. The total phospholipid content was 16 mg/mL.

Vesicle size distribution for the final liposomal preparation and the stability of liposomal preparation were studied over 20 days at +4° C. using both dynamic light scattering (Malvern Autosizer) and laserdiffraction (Malvern Mastersizer). The liposomal preparation was also examined for free crystals of busulphan using electron microscopy. The determination of busulphan concentrations of liposomes was performed using gas chromatography with electron capture detection (Hassan, M., Ehrsson, H. 1983. J Chromatogr 277:374.). These analyses showed that the formed liposomes were unilamellar vesicles with 220±14 nm in diameter. The half-life of busulphan in the present formulation was determined to be 8.7±2.7 days at +4° C. The liposomes in the formulation were stable for 20 days at +4° C., i.e. no aggregates of liposomes were observed as determined by dynamic light scattering and laser diffraction, nor were crystals of free busulphan observed as determined by electron microscopy. The busulphan concentration of the liposomes was 0.31±0.03 mg/mL.

Example 2

Preparation of Liposome-Encapsulated Busulphan Comprising Phosphatidylserine, phosphatidylcholine and cholesterol Materials Phosphatidylserine was obtained from Avanti Polar-Lipids Inc., Alabama USA. Otherwise as in Example 1.

This formulation of liposomal busulphan was prepared as in Example 1, but the lipids phosphatidylserine, phosphatidylcholine and cholesterol in a molar ratio of about 3:7:10 were used.

Analyses (as in Example 1) showed that the formed liposomes were unilamellar vesicles with 290±22 nm in diameter. The half-life of busulphan in the present formulation was determined to be 8 days at +4° C. The liposomes in the formulation were stable for 23 days at +4° C., i.e. no aggregates of liposomes were observed as determined by dynamic light scattering and laser diffraction, nor were crystals of free busulphan observed as determined by electron microscopy. The busulphan concentration of the liposomes was 0.55±0.05 mg/mL.

Example 3

Preparation of Liposome-Encapsulated Busulphan Comprising Cardiolipin, phosphatidylcholine and cholesterol

Materials

Cardiolipin was obtained from Avanti Polar-Lipids Inc., Alabama USA. Otherwise as in Examples 1 and 2.

This formulation of liposomal busulphan was prepared as in Example 1, but the lipids cardiolipin, phosphatidylcholine and cholesterol, in a molar ratio of about 1:4:1.5 were used.

Analyses (as in Example 1) showed that the formed liposomes were unilamellar vesicles with 310±25 nm in diameter. The half-life of busulphan in the present formulation was determined to be 8 days at +4° C. The liposomes in the formulation were stable for 18 days at +4° C., i.e. no aggregates of liposomes were observed as determined by dynamic light scattering and laser diffraction, nor were crystals of free busulphan observed as determined by electron microscopy. The busulphan concentration of the liposomes was 0.61±0.10 mg/mL.

Example 4

Preparation of Liposome-Encapsulated Busulphan Comprising Phosphatidylcholine, cholesterol and stearylamine

Materials

Stearylamine was obtained from Avanti Polar-Lipids Inc., Alabama USA. Otherwise as in Example 1.

This formulation of liposomal busulphan was prepared as in Example 1, but the lipids phosphatidylcholine, cholesterol and stearylamine in a molar ratio of about 7:1:1 were used.

Analyses (as in Example 1) showed that the formed liposomes were unilamellar vesicles with 225±20 nm in diameter. The half-life of busulphan in the present formulation was determined to be 8 days at +4° C. The liposomes in the formulation were stable for 14 days at +4° C., i.e. no aggregates of liposomes were observed as determined by dynamic light scattering and laser diffraction, nor were crystals of free busulphan observed as determined by electron microscopy. The busulphan concentration of the liposomes was 0.75±0.15 mg/mL.

Example 5

Biodistribution of Liposome-Encapsulated Busulphan According to the Invention, Verifying Decreased Toxicity

Distribution of intravenously administered liposomal busulphan (L-Bu), prepared according to Example 1 and hydrated with glucose, and of free busulphan was studied using a C-14 labeled compound. The distribution of $^{14}C$-busulphan entrapped in liposomes was compared with an equal amount of free $^{14}C$-busulphan dissolved in DMSO: ethanol:propyleneglycol (D-Bu) in different organs. Rats were anaesthetized with ether, injected intravenously in the tail-vein with either liposomal $^{14}C$-busulphan (1.5 mL) or $^{14}C$-busulphan (0.25 mL) dissolved in (DMSO: ethanol: propylene glycol in the ratio 0.35:0.25:0.40). The injections of free busulphan were followed by 1.25 mL of saline solution to compensate for the volume differences. At appropriate times (0.17, 0.5, 1, 2, 3, 4, 6, 8, 10, 12, 18, 24 hr) the animals (3 animals for each point of time) were anaesthetized with pentobarbital (50 mg/kg) and blood samples were withdrawn through heart puncture (3-4 mL). Plasma was immediately separated from blood cells at 4000 RPM and stored at −20° C. until analysis. The animals were sacrificed under anesthesia and about 1 g of lungs, heart, liver, brain, spleen, kidney and testis were removed, washed from blood in isotonic saline solution and weighed. The marrow was removed from the femur by flashing with 1 mL of saline solution that was weighed before and after the flushing. The femur was also weighed before and after the flushing (as a control of the marrow weight). All organs were kept at −20° C. before assay either for busulphan concentrations or for the radioactivity distribution. The distribution of the radioactivity that represents busulphan and its metabolites was studied in the organs by liquid scintillation. About 400 mg of each organ were minced and homogenized in 1 mL of saline solution. Duplicates of the homogenized samples (0.4 mL) were transferred into glass counting-vials and solubilized with 1 mL of Soluene-350/isopropanol (1:1) for 2 h at room temperature. To decolorize the samples 0.2 mL of 30% hydrogen peroxide was added after solubilization was completed. The vials were incubated with hydrogen peroxide at 50° C. for 30 min. After cooling 15 mL of Hionic Fluor were added. The vials were kept at room temperature for 2 days to allow chemiluminescence to decay, and then counted for $^{14}C$-radioactivity.

The distribution of the total radioactivity in these organs is listed in Table 1. The radioactivity for both administration forms was calculated as AUC for each organ (1 g) from time 0 to 18 hr after the treatment. As can be seen from Table 1, a significant accumulation (p<0.001) was observed for bone marrow (3 fold) and spleen (2 fold), the target organs for busulphan therapy, after the administration of L-Bu compared with that obtained after the administration of D-Bu. No accumulation in the liver, the main target organ known for busulphan toxicity, was observed. Also a significant (p<0.05) decrease was observed in the distribution of the radioactivity to the heart, lungs, brain and blood, i.e. organs also known to be susceptible to busulphan toxicity. Thus, the improved biodistribution of busulphan, when formulated according to the present invention, optimizes high dose busulphan therapy and decreases its toxicity.

TABLE 1

| Organ | AUC (DPM × $10^4$/g · hr) ±SD | Ratio g organ/g blood | p |
|---|---|---|---|
| Blood D | 9.33 ± 0.08 | 1.00 | 0.02 |
| Blood L | 6.44 ± 0.37 | 1.00 | |
| Marrow D | 18.72 ± 1.45 | 1.96 | 0.006 |
| Marrow L | 60.73 ± 15.48 | 9.42 | |
| Liver D | 11.85 ± 1.95 | 1.27 | 0.78 |
| Liver L | 12.52 ± 3.22 | 1.94 | |
| Spleen D | 9.92 ± 2.81 | 1.06 | 0.008 |
| Spleen L | 21.95 ± 4.17 | 3.41 | |
| Kidney D | 50.87 ± 1.26 | 5.45 | 0.53 |
| Kidney L | 42.97 ± 17.03 | 6.67 | |
| Heart D | 7.93 ± 1.18 | 0.85 | 0.01 |
| Heart L | 4.46 ± 1.46 | 0.69 | |
| Lung D | 9.81 ± 0.63 | 1.05 | 0.03 |
| Lung L | 7.90 ± 0.96 | 1.23 | |
| Brain D | 7.23 ± 1.15 | 0.77 | 0.009 |
| Brain L | 4.21 ± 0.77 | 0.65 | |
| Testis D | 7.77 ± 1.87 | 0.83 | 0.09 |
| Testis L | 5.46 ± 1.18 | 0.85 | |

Example 6

Comparison of the pharmacokinetic Characteristics Between liposome-encapsulated busulphan and busulphan in its Free Form Liposome-encapsulated busulphan (L-Bu) was prepared according to Example 1, and hydrated with aqueous glucose. Pharmacokinetics was studied in a rat model in doses of 0.5-3.5 mg/kg body weight. Means and standard deviations were calculated from the experimental data. The concentration-time curves were adjusted to the data sets via non-linear iterative least square regression analysis. Curve modeling was performed according to the classical one or two compartment open models. The pharmacokinetics parameters were calculated on a PC using WINNONLIN ver 1.5.

The symbols are:

| | |
|---|---|
| BW: | body weight (kg) |
| C0: | intercept at time zero (μg/mL) |
| t∝: | distribution half-life (h) |
| tβ: | elimination half-life (h) |
| Vd: | distribution volume |
| Cp: | concentration in plasma |
| Cl tot: | total body clearance |
| Cbm: | concentration in bone marrow |
| AUC (0-∞): | area under the concentration-time curve, estimated with the trapezoidal rule (μG · hr/mL). |

The statistical analysis (F-test, Student's t-test and variance analysis) was performed using stat-mate (Graph-Pad, version 1.0).

The busulphan in liposomal form was well tolerated at from 0.5 to 3.5 mg/kg. All relevant pharmacokinetic parameters for L-Bu and D-Bu are listed in Table 2.

TABLE 2

| Parameter | Blood (DMSO) | BM (DMSO) | Blood (Lipo) | BM (Lipo) |
|---|---|---|---|---|
| AUC (μg · hr/mL) | 11.82 ± 2.22 | 9.85 ± 0.67 | 9.93 ± 0.15 | 15.82 ± 2.25 |
| t1/2 hr | 1.75 ± 0.37 | 1.53 ± 0.01 | 2.52 ± 0.09 | 3.08 ± 1.06 |
| V (L/kg) | 0.68 ± 0.06 | *0.80 ± 0.10 | 1.39 ± 0.22 | *0.44 ± 0.05 |
| CL (mL · min$^{-1}$) | 0.072 ± 0.004 | 0.66 ± 0.01 | 0.099 ± 0.02 | 0.055 ± 0.03 |

Peak plasma levels were within the range from 833-3538 ng/mL after the administration of D-Bu which is higher than that obtained after the administration of L-Bu (range 1459-2603 ng/mL). Busulphan pharmacokinetics was linear within the range 0.5-3.5 mg/kg for both D-Bu and for L-Bu. The bioavailability for L-Bu as compared with D-Bu (Table 2) was 0.85. However, the distribution of liposomal busulphan to the bone marrow was significantly ($p<0.05$) higher with a ratio 1.6 of AUC marrow/AUC blood compared to 0.90 obtained after the administration of D-Bu.

The distribution volumes of L-Bu were significantly higher (Table 2) compared with those for D-Bu (mean: 1.39 and 0.67 L/kg, respectively). It can also be seen that the apparent distribution volume (Vd×Cp/Cbm) in bone marrow (which reflects the concentration of the drug in bone marrow compared to the concentration of busulphan in plasma) is significantly lower after the administration of L-Bu compared with D-Bu. As it is shown in Table 2, the elimination half-lives was significantly longer in blood and marrow after the administration of L-Bu compared with those obtained after D-Bu. No significant differences were observed in clearance for L-Bu or D-Bu. Thus, liposome-encapsulated busulphan according to the invention exhibits linear pharmacokinetics.

Example 7

Comparison of Myelo-Suppressive Effect Between Orally Administered Busulphan and Intravenously Administered Liposomal Busulphan According to the Invention Liposome-encapsulated busulphan (LB) was prepared according to Example 1, and hydrated with aqueous glucose. Busulphan for oral administration was either suspended in water (Bus/susp) or diluted in acetone as a stock solution which was mixed with water before administration (Bus/Ac). The control group for CFU-GM experiments consists of untreated animals and animals treated by blank preparations containing liposomal solution without busulphan (LC).

Liposomal busulphan was administered through tail vein while the oral forms were administered through gastric tube. The treatment was a conditioning regimen-like schedule with busulphan administration twice a day for 4 days. All doses are presented as mg/kg ±SD. The total doses of busulphan were: LB (20.0±2.0), Bus/susp (21.0±2.1) and Bus/Ac (21.5±1.1).

Bone marrow was harvested on day 1, 3, 6 or 9 after the last dose of the conditioning regimen. Each treatment or control group consisted of a minimum of three animals at each time point.

Mice were sacrificed under general anaesthesia with ether. Both femurs were removed and bone marrow was flushed out under sterile conditions. CFU-GM assay was performed in MethoCult M3530. Briefly: The red cells were lysed with ammonium chloride solution for 10 minutes on ice. Cells were washed twice in PBS and cell number and viability were determined by trypan blue exclusion. Nucleated cells ($1\times10^5$) were plated in 1.1 ml of MethoCult M3530 in 35 mm Petri dishes in triplicates. The plates were placed in 37° C., 5% $CO_2$ and 80% humidity incubator. Colonies >50 cells were counted on the day 7 using an inverted microscope.

As can be seen in FIG. 1, all formulations of busulphan showed a significant decrease in CFU-GM compared with untreated animals. The effect of LB was similar to that obtained after the administration of Bus/Ac. A significant decrease after both treatments was reached on day 3 (40-50% compared with untreated animals) and continued to day 6 and 9. However, a significant difference was observed at the first day of treatment, where the effect of Bus/Ac was higher (expressed as the number of CFU-GM) on the bone marrow compared with that obtained after LB (55% compared to 90%, respectively). Both LB and Bus/Ac had a higher and significant effect on the bone marrow compared with that of busulphan in suspension. The CFU-GM number obtained after treatment with busulphan in suspension was about 75% compared to that obtained in the control group. Mann-Whitney test showed significant p-values when untreated animals were compared with all busulphan treated groups (except LB on day 1). Kruskal-Wallis test showed significant differences among treatment groups compared at the same time point (day 1 p=0.02, day 3 p=0.01, day 6 p=0.0004 and day 9 p=0.008). The administration of liposomes to the mice did not influence the colony forming capacity of the bone marrow and no significant difference was found compared with the CFU-GM obtained from the control group (p>0.05).

Thus, this example demonstrates that no side effects were seen when liposomes were administered alone and that myelo-suppression mediated by the intravenously administered liposomal formulation of busulphan was well comparable with orally administered busulphan, suggesting that the liposomal formulations of busulphan according to the invention are well suited for clinical use.

Example 8

Studies of Pharmacokinetics When Liposome Encapsulated Busulphan is Administered to Humans Eleven patients were included five children and six adults. The patients and diagnosis are shown in Table 3.

TABLE 3

| Patient no. | Age, years | Diagnosis | Dose, mg | AUC | T½, hours | Clearance, L/kg |
|---|---|---|---|---|---|---|
| 1 A | 44 | AML | 6.60 | 567 | 2.21 | 0.16 |
| 2 A | 52 | MDS | 4.90 | 466 | 2.87 | 0.18 |
| 3 A | 33 | AML | 3.60 | 481 | 1.88 | 0.15 |
| 4 A | 57 | CML | 7.30 | 486 | 3.21 | 0.18 |
| 5 A | 55 | MDS | 6.95 | 383 | 3.19 | 0.21 |
| 6 A | 31 | AML | 8.20 | 706 | 2.48 | 0.16 |
| 1 C | 0.83 | SCID | 1.90 | 2621 | 2.23 | 0.15 |
| 2 C | 13 | GCD | 4.84 | 1001 | 3.51 | 0.14 |
| 3 C | 9 | MDS | 5.20 | 2135 | 3.36 | 0.12 |
| 4 C | 8 | AML | 5.15 | 1021 | 2.12 | 0.19 |
| 5 C | 16 | AML | 7.72 | 552 | 2.26 | 0.20 |

The patients received a single dose of liposomal busulphan (2-9 mg). The dose was given one day before their ordinary treatment. The liposomal dose was given as a short infusion (20-40 min).

The liposomal form used in the present study, as well as the method for its manufacture is described in Example 1, i.e. the liposomes have a diameter of 200 nm and the composition is the following: L-α-phosphatidylcholine, 1,2-dioleoyl-sn-glycero-3-phosphate and cholesterol in the molar ratio 9.45:1:9.4.

The present study and the pharmacokinetic analysis showed that:

no significant difference was observed between adult and children in drug clearance at low dose no differences were observed in elimination half life no allergic reaction was observed in any of the patients the formulation is well tolerated for human use no sign of local toxicity was seen during the administration.

Example 9

A Phase II Trial of Liposomal Busulphan as an Intravenous Myeloablative Agent Prior to Stem Cell Transplantation 500 mg/m² as a Optimal Total Dose for Conditioning This example relates to the use of high dose liposomal busulphan administered intravenously in a myeloablative treatment prior to SCT and sets forth the pharmacokinetics of the drug in relation to age, defining an optimal dosage of intravenous liposomal busulphan.

Patients and Methods

Preparation of Liposomal Busulphan

Liposomal busulphan was prepared as follows: Lipids (L-α-phosphatidylcholine, 1,2-dioleolyl-sn-glycero-3-phosphate and cholesterol 9.45:1:9.4) were dissolved in chloroform. Busulphan was added. The mixture of lipids and busulphan was dried by evaporation to a thin film coating the inside of a round glass vessel. Any traces of solvent were removed under a gentle stream of nitrogen. The mixture was then hydrated with glucose (50 mg/ml). Multilamellar vesicles were formed by vortexing the lipid-aqueous mixture. The suspension was transferred to an extruder (Holder with 2 liter capacity, AKA filter, Gottingen, Germany) and extruded five times under nitrogen pressure through 2 stacked polycarbonate filters with pore size of 100 nm. The solution was filtered through a Millex filter (0.22 mm, Millipore GV) and was pyrogen free and sterile. Busulphan concentrations were measured before and after filtration to determine the entrapment efficiency. Busulphan concentration was 0.23±0.03 mg/ml (mean ±SD). Liposomal busulphan was prepared freshly for each patient.

Patients

Between October 1997 and February 2001 a total of 24 patients were enrolled in the study. Eighteen children with median age of 1.3 years (range 0.4-11.5 years) and six adults with a median age of 47 years (range 33.6-55 years) participated in the study. Four children had Hurler's syndrome (MPS type IH), five had acute myeloid leukemia, one had sickle cell disease, one had familial hemophagocytic lymphohistiocytosis (FHL), one had severe combined immuno-deficiency (SCID), one acute lymphoid leukemia, one myelodysplastic syndrome (MDS), one had a relapsed chronic myeloid leukemia, one had Wiskott-Aldrich syndrome and two had chronic myelomonocytic leukemia (CMML). The adult group included three patients with acute myeloid leukemia and three patients with chronic myeloid leukemia. Clinical characteristics of the patients are summarized in Tables 4 and 5. All children and three adults underwent allogeneic stem cell transplantation, while three adult patients underwent autologous stem cell transplantation.

TABLE 4

Characteristics of adult patients

| Pat | Diagnosis | Sex | Age years | Weight kg | Donor | First dose mg/kg | Last dose mg/kg | Total dose mg/m2 | Toxicity | Outcome days |
|---|---|---|---|---|---|---|---|---|---|---|
| A1 | AML | F | 27.5 | 60 | Auto | 1.83 | 2 | 554.00 | Mucositis | 735 |
| A2 | CML | F | 44 | 64 | Auto | 1.92 | 1.92 | 582.00 | Mucositis | 629 |
| A3 | AML | M | 55 | 81 | Allo | 1.85 | 1.67 | 553.00 | | died |
| A4 | CML | M | 50 | 70 | Allo | 1.62 | 1.62 | 488.00 | | died |
| A5 | CML | M | 38 | 96 | Auto | 1.67 | 1.67 | 571.00 | | 529 |
| A6 | AML | F | 55 | 63 | Allo | 2.01 | 2.01 | 608.00 | Mucositis | 516 |

TABLE 5

Characteristics of children

| Patient | Diagnosis | Sex | Age years | Weight kg | Conditioning | First dose mg/kg | Last dose mg/kg | Total dose mg/m2 | Toxicity | Outcome days |
|---|---|---|---|---|---|---|---|---|---|---|
| Ch1 | AML | F | 11.5 | 40 | BuCy | 2.6 | 2.9 | 658 | VOD-I | 545 |
| Ch2 | MPS1 | M | 1.5 | 12.8 | BuCy | 2.2 | 2.3 | 442 | | 525 |
| Ch3 | MDS | M | 1 | 8.5 | BuCy | 2.2 | 2.1 | 371 | | 565 |
| Ch4 | SCID | M | 0.5 | 7.7 | BuCy | 1.2 | 1.2 | 200 | | 492 |
| Ch5 | CML | M | 4 | 15 | BuCy | 2 | 2.13 | 378 | | 786 |
| Ch6 | MPS1 | F | 2.9 | 13.3 | BuCy | 2.12 | 2.12 | 402 | | Re-SCT |
| Ch7 | FHL | M | 0.4 | 6 | BuCy | 2.33 | 2.33 | 374 | Mucositis | 691 |
| Ch8 | CMML | M | 0.4 | 6.4 | BuMelCy | 2.13 | 2.25 | 400 | | died |
| Ch9 | CMML | M | 1 | 9.5 | BuMelCy | 1.84 | 1.89 | 360 | | died |
| Ch10 | MPS1 | M | 0.75 | 10 | BuCy | 1.8 | 1.8 | 327 | | 621 |
| Ch11 | MPS1 | M | 1.5 | 13 | BuCy | 2.7 | 3 | 519 | | 426 |
| Ch12 | AML M1 | M | 9 | 27.5 | BuCy | 2.1 | 1.9 | 412 | | 352 |
| Ch13 | sickle cell disease | M | 2.5 | 12.5 | BuCy | 2.1 | 2.3 | 408 | | 432 |
| Ch14 | AML | F | 1.1 | 8.7 | BuCy | 2.5 | 2.5 | 452 | | 308 |
| Ch15 | AML | F | 0.5 | 6.4 | BuCy | 2.56 | 2.25 | 366 | Mucositis | 286 |
| Ch16 | Wiskott-Aldrich | M | 6.17 | 17 | BuCy | 2.5 | 2.6 | 503 | | 229 |
| Ch17 | AML | M | 0.75 | 9.6 | BuCy | 2.8 | 2.2 | 459 | VOD-II | 252 |
| Ch18 | AML | F | 10.6 | 36.4 | BuCy | 2.2 | 2.2 | 518 | | 203 |

Treatment

The conditioning regimen consisted of liposomal busulphan and cyclophosphamide. Two children with CMML received additional treatment with melphalan (140 mg/m² of body surface). Liposomal busulphan was administered twice daily. All children and three adult patients received totally 8 doses over four days and three adult patients received 4 doses over two days followed by oral busulphan for the next two days. All patients received about 2 mg/kg, except of one child (Ch4) who received 1 mg/kg according to the treatment protocol. The first dose calculated on the basis of BSA was 560±40 mg/m² for adults and 432±81 mg/m² for children. To minimize the risk of chronopharmacologic variation, busulphan was given at $8^{00}$ AM and $8^{00}$ PM. Liposomal busulphan was administered as two hours infusion for adults and three hours infusion for children.

Clonazepam (1.5 mg/day first two days and 3 mg/day at day three and four for adults while children received 0.3 mg/day for two days followed by 0.6 mg for the next two days) was given to all patients as prophylaxis against seizures. All patients undergoing allogeneic stem cell transplantation received methotrexate and cyclosporine as graft versus host disease (GVHD) prophylaxis. Methotrexate was administered at day +1, +3, +6 and +11 in a dose of 15, 10, 10 and 10 mg per square meter of body surface, respectively. Cyclosporine was given as either 3 mg/kg or 5 mg/kg at day −1 followed by 1 mg/kg or 3 mg/kg, respectively, from day 0 with the aim to keep therapeutic concentrations between 100 and 300 ng/ml depending on the donor type.

Pharmacokinetics

Blood samples were collected in heparinized tubes before the infusion, 15, and 30 minutes after the infusion start, at the end of infusion and at 3, 5, 15, 30, 60, 120, 180, 240, 360, 480 and 600 minutes after the end of infusion. Plasma was immediately separated and stored at −20° C. until assayed. Plasma samples were thawed before analysis. The appropriate plasma volumes (0.5-1 ml) was transferred to new tubes and sodium iodide (1 ml, 8M), internal standard (1,5-bis(methanesulphonyloxy)pentane; 500 ng in 50 μl acetone) and n-heptane (0.4 ml) were added. Busulphan and the internal standard were reacted with sodium iodide for 45 min at 70° C. under gentle stirring to form 1,4-diiodobutane and 1,5-diiodopentane. The heptane phase was taken to analysis using a gas chromatograph with electron capture detection. The calibration curve using spiked plasma was linear within the range of 10-2600 ng/ml. Busulphan concentrations were calculated using Star integration program (Varian, Walnut Creek, Calif., USA).

Busulphan concentration-time data were adjusted to a two-compartment open model using Gauss-Newton (Levenberg-Hartly) criteria. Parameters such as the distribution volume of the central compartment, the elimination rate constant, the plasma maximum concentration and the microconstants were estimated. The clearance (Cl) and distribution volume at the steady-state were calculated from the primary parameters. The plasma-concentrations versus time curves (AUC) were calculated from the model derived parameters and the elimination half-lives were calculated from the slope of the terminal phase of elimination.

The pharmacokinetic modeling was performed using WinNonlin version 3.0 (Pharsight, Mountain View, Calif., USA). The mean, median and standard deviations were calculated using GraphPad, InStat (version 3.0, Graph Pad, San Diego, Calif., USA). All values are presented as mean ±SD. Statistical analysis was performed using the Kruskal-Wallis test (non-parametric ANOVA) and Mann-Whitney's U-test (non-parametric, unpaired, two-tailed) whenever appropriate.

Diagnosis of VOD, Mucositis and GVHD, Including Scoring of Severity

Veno-occlusive disease (VOD) was diagnosed on the basis of clinical criteria—i.e. presence of hyperbilirubinemia (total serum bilirubin >34 tμmol/L) and development of two of the following signs during the first 21 days post-transplant: weight gain >5% from preconditioning baseline weight, ascites and/or hepatomegaly. VOD severity was graded as mild (self-limited and required no treatment), moderate (clinical abnormalities which required pain control and/or diuretics for fluid retention) and severe VOD (clinical abnormalities which required therapy and did not resolve by day 100 post transplant or ended by death). Mucositis was scored (I, II and III), according to Bearman (Bearman S I, Appelbaum F R, Buckner C D, et al: Regimen-related toxicity in patients undergoing bone marrow transplantation. J Clin Oncol 6:1562-8., 1988). The diagnosis and clinical grading of GVHD were based on Glucksberg's criteria (Glucksberg H, Storb R, Fefer A, et al: Clinical manifestations of graft-versus-host disease in human recipients of marrow from HL-A-matched sibling donors. Transplantation 18:295-304., 1974).

Results

Clinical Outcome

The clinical outcome of the patients is shown in Tables 4 and 5. All patients became neutropenic following the administration of liposomal busulphan and cyclophosphamide with or without melphalan. The median time to neutrophil engraftment (>0.5×$10^9$/L) was 11 days (range 9-21) for the children and 14 days (range 11-29) for the adults. The median time to platelet recovery of >20×$10^9$/L and >50× $10^9$/L was 15 days (range 3-32) and 28 days (range 3-86), respectively. Both children with CMML died during six months after transplantation. One child died because of an EBV related lymphoma at day +58 and the second child died 180 days post transplantation of gastrointestinal hemorrhage caused by GVHD. Two adult patients who underwent autologous transplantation died from disease progression, on day +45 and +60 after transplantation, respectively. At the time of evaluation with a median follow up of 18 months, 20 patients were alive. Of four patients with Hurler's syndrome one had about 30% donor chimerism, the second child was re-transplanted using melphalan and cyclophosphamide due to rejection, and the other two were fully chimeric. The children who had a low grade of chimerism also had lower exposure of busulphan expressed as AUC compared with the other two. The children with AML, ALL, CML and MDS were in complete remission, 6 were fully chimeric and 2 mixed chimeras. The children transplanted for FHL, SCID, Wiscott-Aldrich syndrome and sickle cell disease were alive, well and three of them fully chimeric. Four of six adult patients were alive, well and fully chimeric.

Toxicity

Liposomal busulphan was well tolerated, none of the patients died of regimen related toxicity. One patient experienced a mild VOD with maximum bilirubin of 58 μmol/l, ascites and increase in weight. This patient (Ch1) received 2.5 mg/kg×2 because of her aggressive disease; her AUC was 12879 and 12076 ng/ml.hr for first and last dose respectively. One child (Ch17) with AML had moderate grade VOD with maximum bilirubin of 111 μmol/l, increase in weight and hepatomegaly (AUC's for first and last dose were 14324 and 9057 ng/ml.hr, respectively). Moreover, two children showed elevated serum bilirubin but did not fulfill the criteria of VOD. Ultrasound examination did not show any change in the liver blood flow. Both these patients (CMML) received additionally melphalan as a part of their conditioning. Six patients developed a mucositis grade II. Two of these patients required additional parenteral nutritional support. Nausea and vomiting was seen in the patient who received 2.6 mg/kg twice a day; otherwise no sign of nausea or vomiting was observed. All patients received clonazepame as prophylaxis and none of the patients experienced seizures or other neurological toxicity. No renal or bladder toxicity was observed.

Pharmacokinetic Analysis

The data from the pharmacokinetic analysis are summarized in Table 6.

TABLE 6

Pharmacokinetic data for adults and children after the first and the last dose

| Parameter | | Children | Adults | p Value |
|---|---|---|---|---|
| Age | | | | |
| Median | | 1.3 | 47 | |
| Range | | 0.4-11.5 | 27.5-55 | |
| First dose (mg/kg) | mean ±SD | 2.22 ± 0.38 | 1.82 ± 0.18 | |
| Last dose (mg/kg) | mean ±SD | 2.22 ± 0.41 | 1.82 ± 0.15 | |
| AUC first dose (ng/ml · hr) | mean ±SD | 9381 ± 1510 | 13010 ± 1460 | <0.001 |
| AUC last dose (ng/ml · hr) | mean ±SD | 8919 ± 1825 | 13864 ± 777 | <0.001 |
| Elimination first dose (hr) | mean ±SD | 2.59 ± 0.54 | 3.35 ± 0.44 | |
| Elimination last dose (hr) | mean ±SD | 2.72 ± 0.59 | 3.61 ± 0.74 | |
| Distribution half-life first dose (hr) | mean ±SD | 0.38 ± 0.27 | 0.29 ± 0.18 | NS |
| Distribution half-life last dose (hr) | mean ±SD | 0.36 ± 0.29 | 0.29 ± 0.21 | NS |

TABLE 6-continued

Pharmacokinetic data for adults and children after the first and the last dose

| Parameter | | Children | Adults | p Value |
|---|---|---|---|---|
| Cl fist dose (ml/min/kg) | mean ± SD | 3.61 ± 0.62 | 2.40 ± 0.29 | |
| Cl last dose (ml/min/kg) | mean ± SD | 3.79 ± 0.62 | 2.32 ± 0.22 | <0.0001 |
| Cl first dose (ml/min/m2) | mean ± SD | 85.3 ± 13.8 | 92.6 ± 10.9 | NS |
| Cl last dose (ml/min/m2) | mean ± SD | 91.3 ± 18.8 | 89.9 ± 12.6 | NS |
| VD first dose (L/kg) | mean ± SD | 0.68 ± 0.16 | 0.55 ± 0.12 | |
| VD last dose (L/kg) | mean ± SD | 0.72 ± 0.19 | 0.59 ± 0.10 | |

Figure 2:
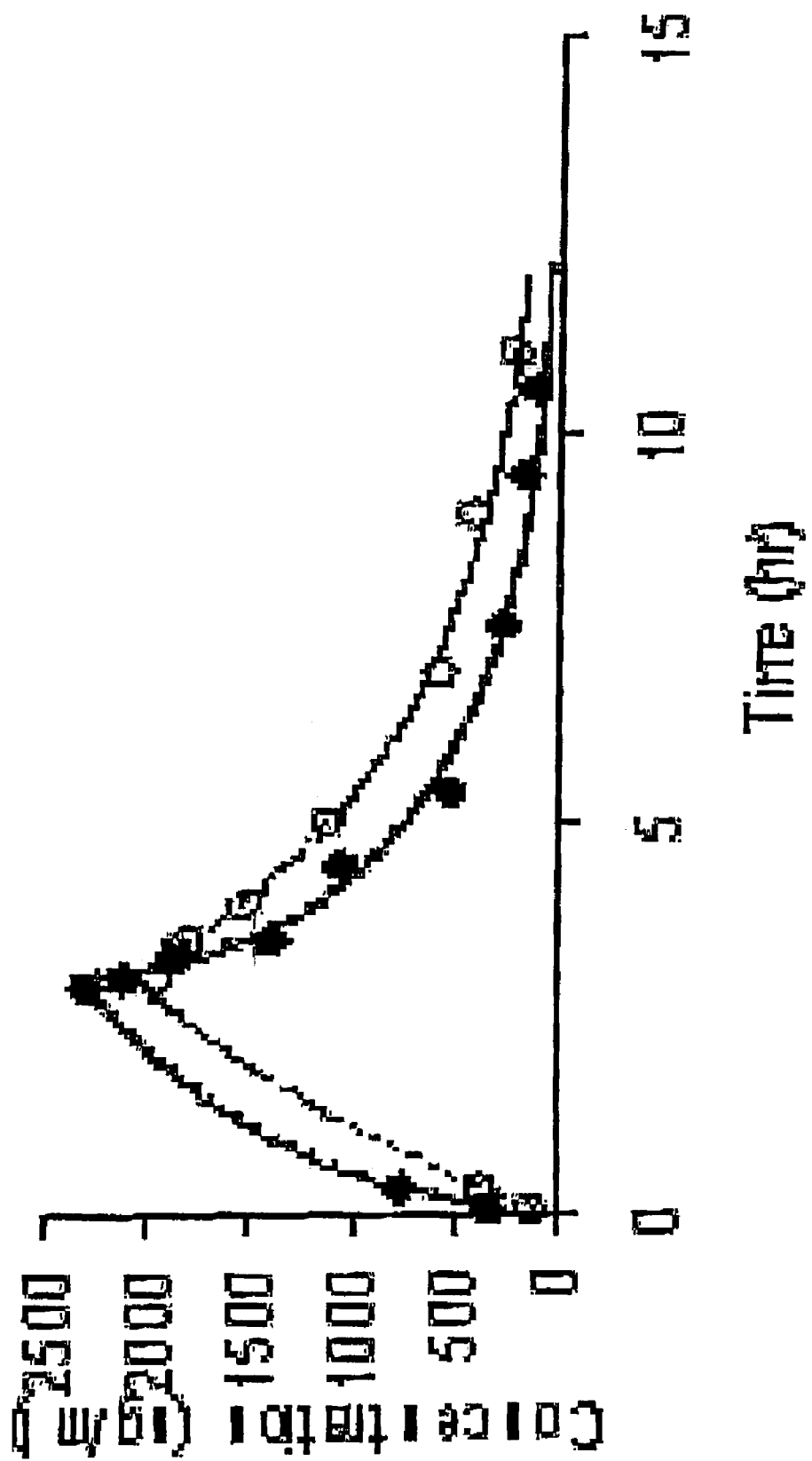
FIG. 2. Plasma time concentration curve in adult patient (A6) receiving eight doses of liposomal busulphan. Solid line and filled circles represent the first dose while the dashed line and open circles represent the eighth dose.
Figure 3:
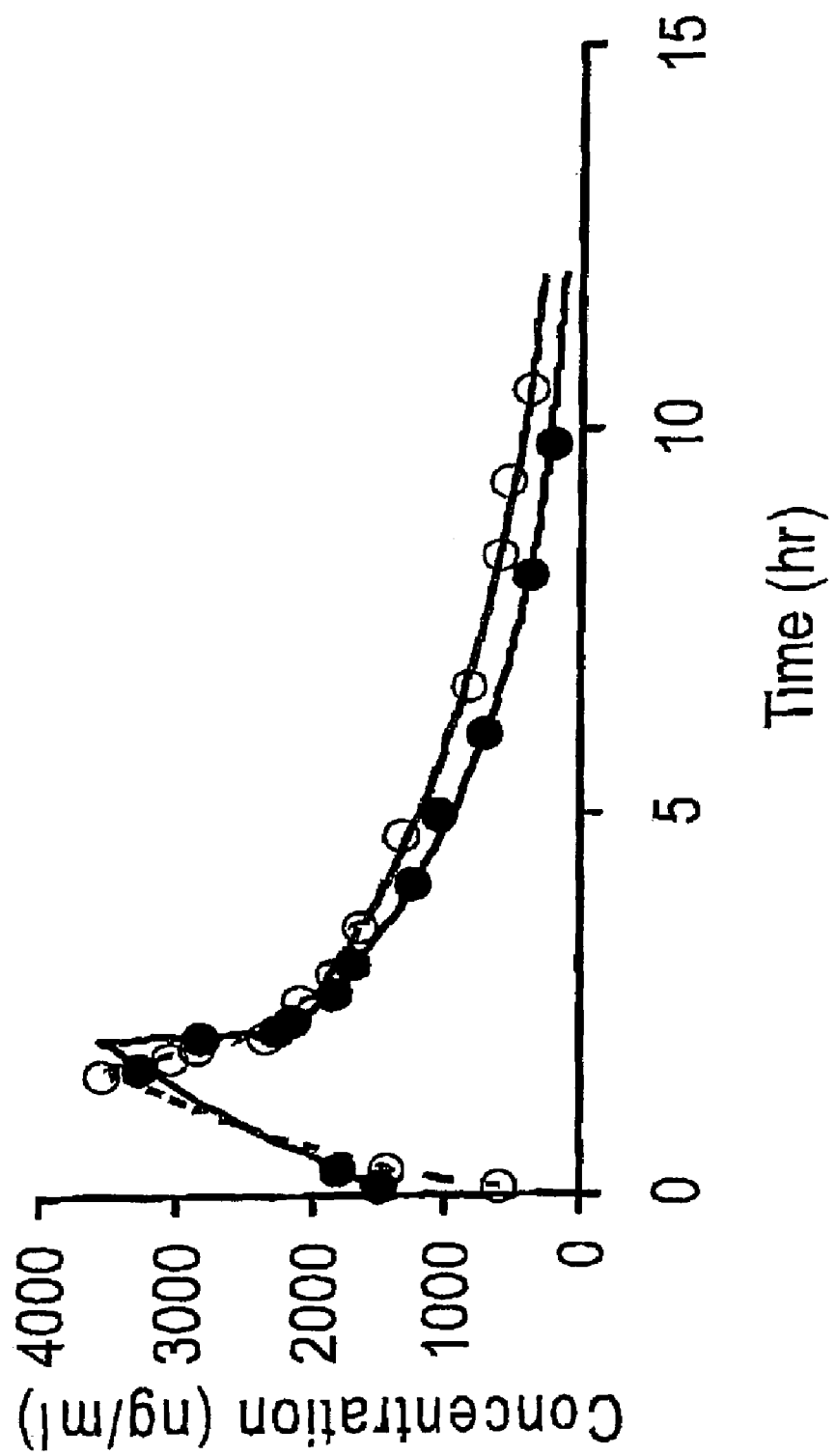
FIG. 3. Plasma time concentration curve in child (Ch14) receiving eight doses of liposomal busulphan. Solid line and filled circles represent the first dose while the dashed line and open circles represent the eighth dose.

FIGS. 2 and 3 show examples of the plasma concentrations (ng/ml) over the time curve in one adult and one child patient after the first and the last dose.

Area Under Concentration Versus Time Curve

The AUC was measured after the first dose and the last dose in all twenty-four patients (fourth dose in three and eighth dose in twenty-one). The mean AUC (corrected for 2 mg/kg) in children was 9381 ng.hr/ml (SD 1510 ng.hr/ml) after the first dose and was 8919 ng.hr/ml (SD 1825 ng.hr/ml) after the last dose. The variation of AUCs in children was 16% for the first dose and 20% for the last dose. The lowest AUCs were observed in patients with Hurler's disease. The mean AUC in adult patients was 13010 ng.hr/ml (SD 1460 ng.hr/ml) after the first dose and 13864 ng.hr/ml (SD 777 ng.hr/ml) after the last dose. The inter-patient variation between adults was 11% for the first dose and 6% for the last dose when the dose was corrected to 2 mg/kg.

No significant difference was observed between the first and the last dose in both children and adults. The AUC corrected for 2 mg/kg was significantly ($p<0.01$) higher in adults compared to children after the first and the last dose.

Maximum Concentration (Cmax)

The calculated Cmax in children ranged from 1261 to 3277 ng/ml for the first dose with a mean of 2451 ng/ml (SD 494 ng/ml) and from 894 to 3505 ng/ml with a mean of 2253 ng/ml (SD 635 ng/ml) for the last dose. The calculated Cmax in adult patients ranged from 1913 to 3517 ng/ml with the mean of 2536 ng/ml (SD 607 ng/ml) for the first dose and from 2049 to 3090 ng/ml with the mean of 2732 ng/ml (SD 361 ng/ml) for the last dose. There were no significant differences between the first and the last dose either in children or in adults and no difference was found comparing children and adults.

Distribution Volume, Clearance and Elimination Half-Life

Figure 4:
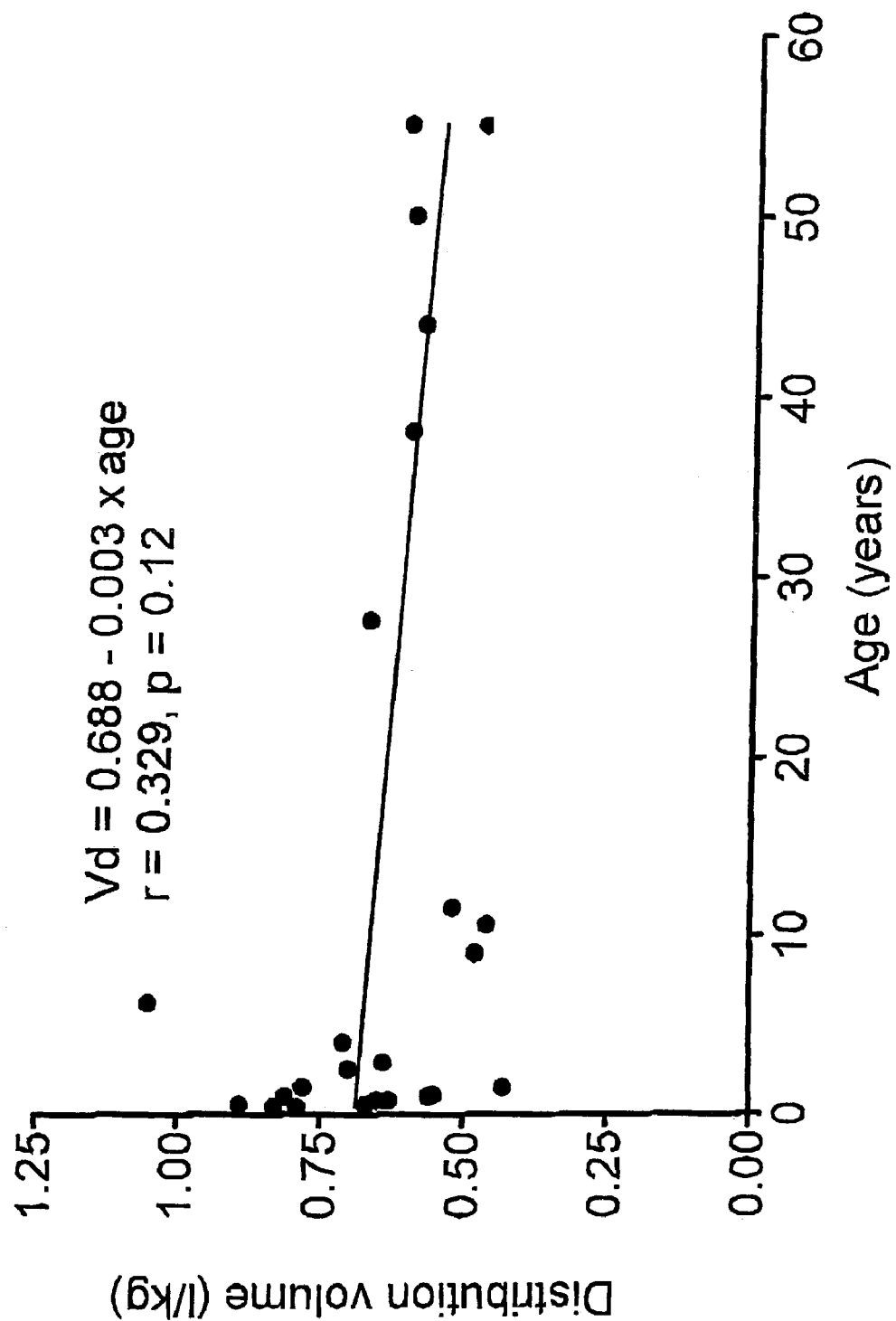
FIG. 4. The correlation between distribution volume (Vd) corrected for body weight (kg) and age after the first dose of liposomal busulphan. The solid line is the regression line. The correlation between distribution volume corrected for body weight and age after the last dose was (Vd=0.74+ 0.003×age, r=0.376, p=0.07).

In children, the calculated distribution volume was 0.68 L/kg (SD 0.16 L/kg) after the first dose and was not significantly different from that calculated after the last dose (mean 0.73 and SD 0.18 L/kg). In adult patients the distribution volume was 0.55 L/kg (SD 0.13 L/kg) for the first dose and 0.59 L/kg (SD 0.06 L/kg) for the last dose. No significant difference between the first and the last dose was observed in adults. No significant correlation between distribution volume and age was found after the first dose (FIG. 4), however, a tendency ($p=0.07$) in correlation between the distribution volume and age was observed after the last dose. Similar tendency ($p=0.07$) was observed when children were compared to adults (Table 6).

Figure 5:
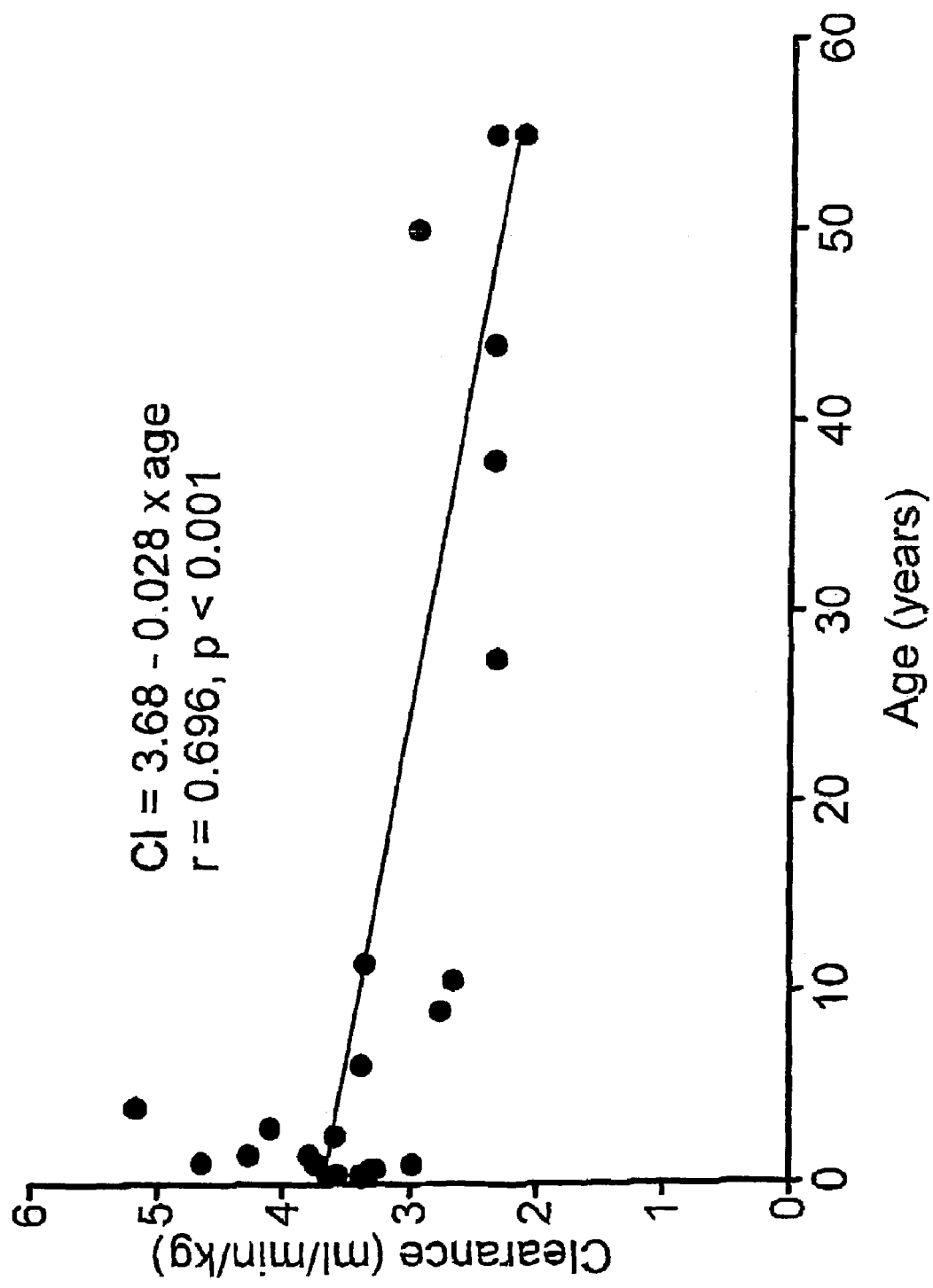
FIG. 5. The relationship between clearance (Cl) corrected for body weight (kg) and age after the first dose of liposomal busulphan. The solid line is the regression line. The correlation between clearance corrected for body weight and age after the last dose was (Cl=3.88+0.033×age, r=0.762, p<0.0001).
Figure 6:
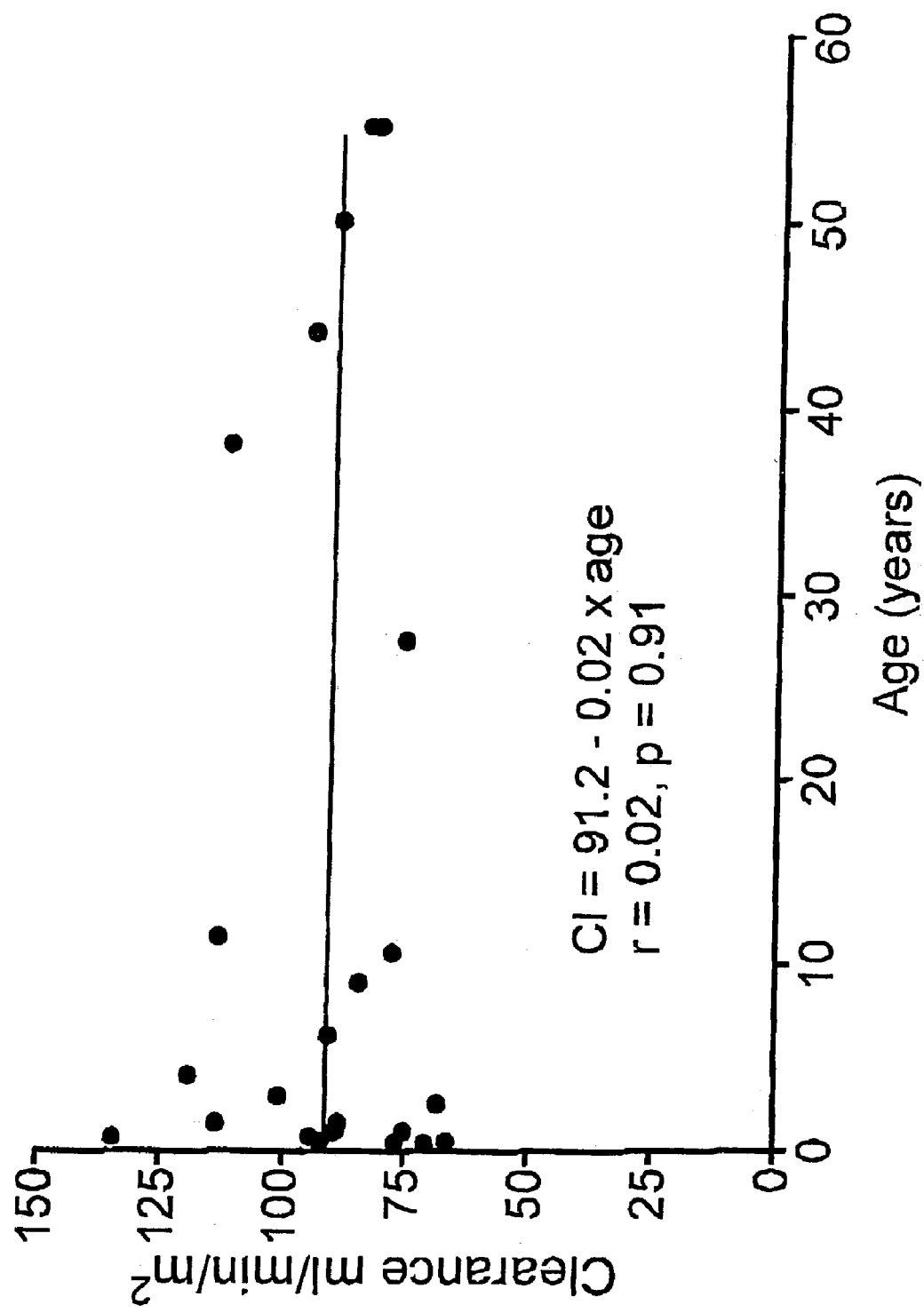
FIG. 6. The relationship between clearance (Cl) corrected for body surface area ($m^2$) and age after the first dose of liposomal busulphan. The solid line is the regression line. The correlation between clearance corrected for body surface and age after the last dose was (Cl=84.2+0.19×age, r=0.27, p=0.19).

The clearance calculated per kg of body weight after the first dose in children did not differ from that calculated after the last dose of 3.61 ml/min/kg (SD 0.62 ml/min/kg) and 3.79 ml/min/kg (SD 0.63 ml/min/kg), respectively. No difference was observed in adults between the first and the last dose of 2.40 ml/min/kg (SD 0.29 ml/min/kg) and 2.33 ml/min/kg (SD 0.22 ml/min/kg), respectively. However, clearance was significantly ($p<0.001$) higher in children compared to adults after both the first and the last dose. There was significant correlation between age and clearance as shown in FIG. 5. When the clearance was calculated on the basis of surface area, no significant difference was found between adults and children either after the first dose (85.3 and 92.6 ml/min/m$^2$, respectively) or after the last dose (91.3 and 98.9 ml/min/m$^2$, respectively). The regression analysis did not show any correlation between age and clearance corrected for body surface area (FIG. 6).

The elimination half-lives for children after the first and the last dose (mean 2.59, SD 0.54 hr and mean 2.72, SD 0.59 hr, respectively) showed no significant difference. The elimination half-lives in children after both the first and the last dose were significantly shorter compared to that observed in adults (mean 3.35, SD 0.44 hr and mean 3.61, SD 0.74 hr, respectively).

The inter-patient variation in drug exposure expressed as AUC after the intravenous administration of liposomal busulphan was low in adult patients (11% and 6% after first and last dose respectively). This may reduce the drug related toxicity by decreasing the wide inter-patient variability. The mean AUC obtained in adult patients after a dose of 0.9 mg/kg was 5890 ng.hr/ml.

Children showed about 50% higher clearance compared to adults. Busulphan clearance was age dependent after the intravenous administration of liposomal busulphan (FIG. 5). No difference between adults and children was found after the first dose or the last dose, when the clearance was corrected to body surface rather than body weight (Table 6) and no correlation between clearance corrected for body surface area and age was found (FIG. 6). Busulphan has been shown to be highly trapped and metabolized in the liver. A possible explanation for the difference observed between adults and children when the drug is dosed per kg body weight after intravenous administration is the difference in liver volume. The distribution volume observed in the present study showed a tendency to be higher in children compared to adults (about 0.70 and 0.55 L/kg, respectively).

A significant difference in elimination half-lives between adults and children was found for both the first and the last dose.

A low rate of toxicity was observed in the present study, despite higher doses of busulphan given to younger children. Nausea and vomiting was seen in one child, who received 2.6 mg/kg twice a day. This patient developed a mild VOD that was self-limited and did not require any treatment. Another patient experienced a moderate grade of VOD that resolved after defibrotide and intensive care treatment. The two patients, who experienced VOD, were both heavily pretreated for their disease. With the exception of a low number of patients with mucositis (20%) grade II, no other organ toxicity was observed.

It is clear that busulphan pharmacokinetics is age dependent. Busulphan belongs to the very few anticancer drugs for which the body weight is still the basis of dosage. An adjustment of the dosage to body surface area will increase the given dose to young children by about 35%. The AUC obtained after an intravenous dose of 1 mg/kg was 30% lower in children compared to adults indicating that a dosage based on body surface area should be used. An increased dosage to children will increase the systemic and marrow exposure to busulphan.

A mean AUC of 6100 ng.hr/ml was obtained after the administration of 0.9 mg/kg to adult patients. However, the administration of 1.1 mg/kg to children resulted in a mean AUC of 5100 ng.hr/ml, which is about 20% lower than that seen in adults. The administration of 0.8 mg/kg to adults will reduce the AUC to approximately 5500 ng.hr/ml. Thus, a dose of 0.8 mg/kg four times a day for four days in adults is equal to a total dose of 500 mg/m$^2$. For the children a dose of 500 mg/m$^2$ will increase the dose by about 35-50%, which is equal to the difference observed in clearance between adults and children. The total myeloablative AUC over the conditioning regimen (based on 500 mg/m$^2$ of intravenous busulphan) is 88000 ng.hr/ml.

An age dependent pharmacokinetics after the administration of intravenous liposomal busulphan was observed. An optimal dose of 500 mg/m$^2$ to children will allow a mean systemic exposure equal to that seen in adults without increasing the risk for serious and/or life threatening toxicity.

Example 10

Preparation of a Liposomal Composition Comprising Busulphan and N-Acetyl-L-Cysteine Liposomal busulphan was prepared using L-α-phosphatidylcholine, 1,2-dioleolyl-sn-glycero-3-phosphate and cholesterol. L-α-phosphatidylcholine (EPC), 1,2-dioleolyl-sn-glycero-3-phosphate (DOPA) and cholesterol in the molar ratio 9.45:1:9.4 were dissolved in chloroform. Busulphan dissolved in dichloromethane was added. The mixture of lipids and busulphan was dried by evaporation to a thin film coating the inside of a round glass vessel. Any traces of solvent were removed under a gentle stream of nitrogen. The mixture was then hydrated with 43.75 mL of glucose solution (50 mg/mL, pH 4.0) and 6.25 ml of N-acetyl-L-cysteine (200 mg/ml) (Tika) was added. Multilamellar vesicles were formed by vortexing the lipid-aqueous mixture for 10 minutes at room temperature. The suspension was transferred to an Extruder (LiposoFast 50, Avestin, Ottawa, Canada) and extruded under nitrogen, through 2 stacked polycarbonate filters of 100 nm pore size 5 times. All these preparations were performed under aseptic conditions. Busulphan concentrations were determined before and after filtration to determine the entrapment efficiency. The total phospholipid content was 16 mg/mL Busulphan concentration was determined to 0.25 mg/ml. NAC was evenly distributed into the inside of liposomes and within the solution with a concentration on 25 mg/ml.

Example 11

The Effect of Modulation of GSH Cellular Content on Busulphan-Induced Cytotoxicity in Hematopoietic Cells In Vitro and In Vivo The example refers to an investigation of the effect of modulation of cellular GSH on busulphan cytotoxicity in hematopoietic cells. The experimental study comprises three parallel systems, normal human bone marrow and a human leukemic cell line in vitro, and a mice model in vivo. The example shows that increased intracellular levels of GSH does not affect busulphan-induced cytotoxicity in CD34+ progenitor cells in vitro. This has not previously been studied in hematopoietic progenitor cells, but N-acetylcysteine has been shown to protect CFU-GM from normal bone marrow against radiation (Selig, C., Nothdurft, W., and Fliedner, T. M. Radioprotective effect of N-acetylcysteine on granulocyte/macrophage colony-forming cells of human bone marrow. J Cancer Res Clin Oncol, 119: 346-349, 1993.).

Volunteers, Materials and Methods

Bone Marrow Volunteers and CD34+ Cells Separation

Ten healthy volunteers were recruited after a medical interview. The study followed the guidelines of the local authorities and was approved by the local ethical committee. Approximately 10-15 ml of bone marrow was aspirated in local anaesthesia from spina illiaca anterior superior, and mononuclear cells were separated by density gradient centrifugation on ficoll. CD34+ cells were separated on a MACS system by positive selection using CD34+ Separation Kit according to the manufacturer's instructions. Cells were incubated in RPMI-1640 medium supplemented with 10% heat inactivated fetal bovine serum at 37° C. in a humidified 5% CO$_2$ atmosphere. Cells used for pharmacodynamic study were incubated in busulphan of final concentrations of 1, 2.5, 5, 10, 20, 40 or 60 µg/ml for 2, 4 or 8 hours. Cells used for the GSH modulation part were treated with N-acetyl-L-cysteine (NAC) (1 mM) or L-buthionine-[S,R]-sulfoximine (BSO) (50 µM) for 16 to 18 hours, followed by busulphan in final concentrations of 4.5 or 10 µg/ml for 4 hours. After incubation, cells were washed and plated for clonogenic assay.

Materials

The following materials were used in the study: RPMI-1640, Iscove's modified Dulbecco's medium, phosphate buffer saline, penicillin/streptomycin, fetal bovine serum (Life Technologies A B, Täby, Sweden); MethoCult™ GF H4434 and MethoCult™ GF M3534 (Metachem Diagnostics Ltd., Piddington, UK); CD34+ Separation Kit (Miltenyi Biotec GmbH, Bergisch Gladbach, Germany); Lymphoprep (Nycomed, Oslo, Norway); [$^3$H]Thymidine (Amersham Pharmacia Biotech UK Ltd., Buckinghamshire, UK); cholesterol, L-α-phosphatidylcholine and 1,2-dioleolyl-sn-glycero-3-phosphate (Avanti Polar-Lipids Inc., Alabaster, Ala., USA); Sodium chloride 9 mg/ml (Fresenius Kabi, Uppsala, Sweden); glucose 50 mg/ml (Pharmacia-Upjohn, Uppsala, Sweden). Other chemicals were purchased from Sigma, Chemical Co, St. Louis, Mo., USA.

Animals and Treatment

Balb/c mice were purchased from B&K Universal Limited, Sweden. Female mice were 6 to 12 weeks old with a weight ranging from 20 to 24 g. Local animal ethical committee approved animals housing conditions and experimental design. Animals were fed with standard pelleted food and water ad libitum. Animals were treated once a day for 4 consecutive days. Treatment consisted of N-acetyl-L-cysteine (1.38±0.07 mmol/kg) orally or L-buthionine-[S,R]-sulfoximine (0.93±0.03 mmol/kg) intraperitoneally followed by liposomal busulphan (37±1.4 mg/kg) intraperitoneally. Animals were sacrificed at day 1, 3, 6, 9 or 12 after the last dose of treatment.

Cell Line

The P39 cell line was kindly provided by Prof. Y. Yoshida, Center for South East Asian Studies, Kyoto University, Kyoto, Japan. Cells were cultured in RPMI-1640 medium supplemented with 10% heat inactivated fetal bovine serum (FBS), penicillin (25 IU/ml) and streptomycin (25 µg/ml) at 37° C. in a humidified 5% $CO_2$ atmosphere. Exponentially growing cells were used in all experiments. Cells were incubated with N-acetyl-L-cysteine (1 mM) or L-buthionine-[S,R]-sulfoximine (50 µM) for 16 to 18 hours and then with busulphan in final concentrations of 10, 20 or 40 µg/ml for 4 hours. After incubation, cells were washed and re-cultured in busulphan-free medium for 72 hours.

Preparation of Busulphan

Busulphan for in vitro studies was diluted in sterile dimethyl sulfoxide (DMSO) and then in medium before addition to cell suspension. The final concentration of DMSO was 0.05% for CD34+ cells and 0.2% for P39 cells.

Liposomal busulphan was used in the in vivo study and prepared as described in example 1. Liposomal busulphan was prepared freshly before each experiment and stored in refrigerator until use.

In Vitro Pharmacokinetics

Concentration of busulphan at the end of incubation was calculated as $C=C_0 \cdot e^{-kt}$ (half-life in RPMI-1640 medium at 37° C. 16 hours, k=0.043) and AUC was calculated according to the trapezoidal rule.

Clonogenic Assay

CD34+ cells were treated with NAC, BSO, DMSO or busulphan alone or in combinations, washed and 2000 cells were plated in 1.1 ml of MethoCult™ GF H4434 in 35 mm Petri dishes in triplicates. Colonies were scored on day 14 using an inverted microscope. Murine bone marrow was harvested on day 1, 3, 6, 9 or 12 after the last dose of the treatment. Control group and each treatment group consisted of a minimum of three animals at each time point. Mice were sacrificed under general anaesthesia. Both femurs were removed and bone marrow was flushed out under sterile conditions. Cells were counted in Türk solution and nucleated cells ($0.5 \times 10^5$) were plated in 1.1 ml of MethoCult™ GF M3534 in 35 mm Petri dishes in triplicates. The plates were placed in incubator (37° C., 5% $CO_2$ and 100% humidity). CFU-GM, equal to or more than 50 cells, were counted on the day 7 using an inverted microscope.

Proliferation, Clonogenicity and Apoptosis in P39 Cells

Proliferation was assessed using the [$^3$H]thymidine incorporation assay. Clonogenic capacity was determined in 0.9% methylcellulose and apoptosis with morphology in May-Grünwald-Giemsa staining as described in (Hassan, Z., Hassan, M., and Hellstrom-Lindberg, E. The pharmacodynamic effect of busulfan in the P39 myeloid cell line in vitro. Leukemia, 15: 1240-1247, 2001).

GSH Assay and Protein Quantification

Intracellular concentrations of GSH were determined using the enzymatic assay according to Tietze (Tietze, F. Enzymic method for quantitative determination of nanogram amounts of total and oxidized glutathione: applications to mammalian blood and other tissues. Anal Biochem, 27: 502-522., 1969). Total cellular protein was assessed according to Lowry after dissolving the precipitate in 1M NaOH (Lowry, O. H., Rosebrough, N. J., Farr, A. L., and Randall, R. J. Protein measurement with the folin phenol reagent. J Biol Chem, 193: 265-275., 1951)

Results

Pharmacodynamic Effect of Busulphan on CD34+ Cells

Figure 7A:
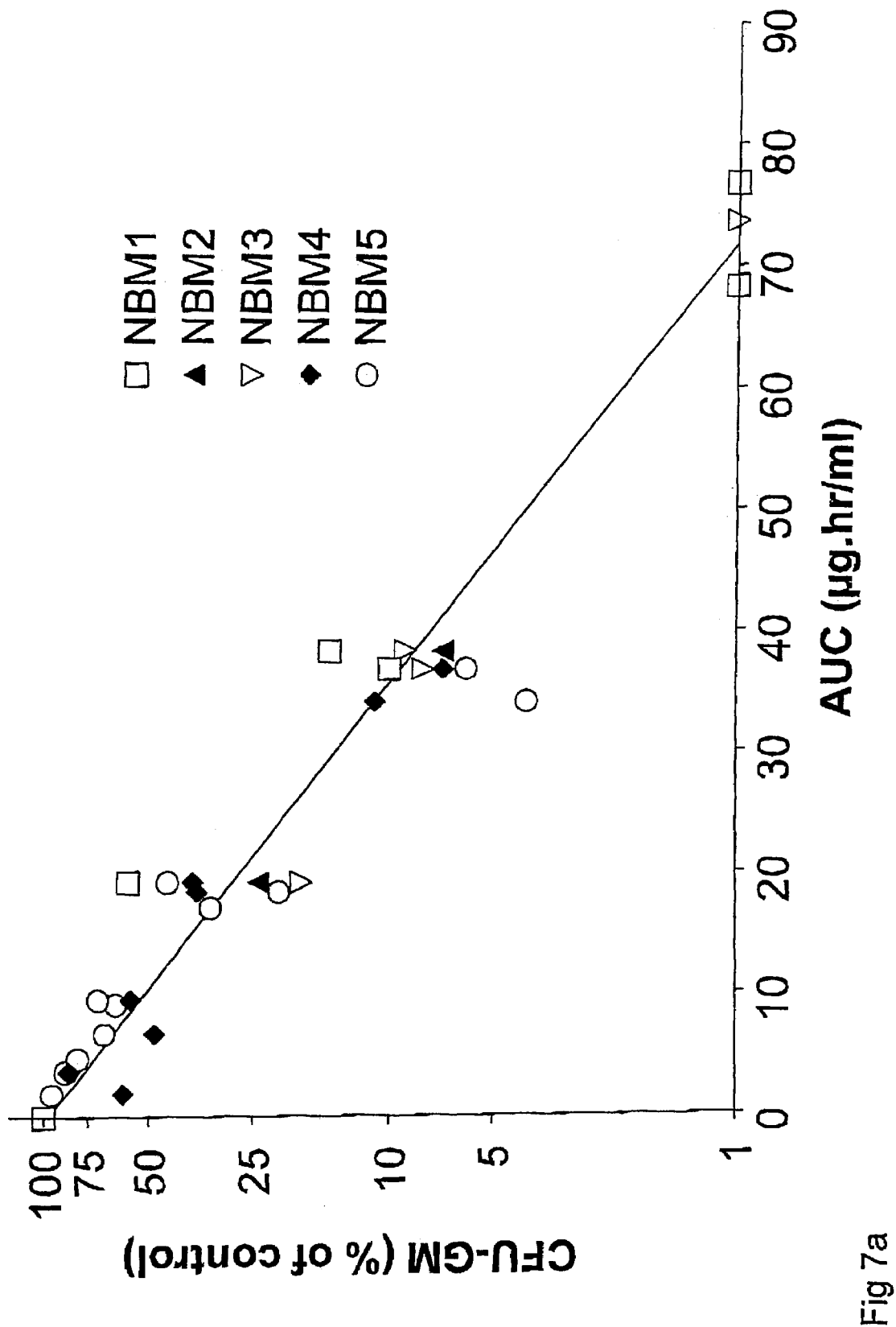
FIG. 7a. Surviving fraction of CFU-GM (colony forming-unit granulocyte-macrophage) related to AUC. CD34+ cells were separated from five healthy volunteers, incubated with busulphan and plated in methylcellulose medium. CFU-GM were counted on day 14. Results are expressed as a percent-age of control. Compact line represents linear regression on all points. AUC is expressed as μg.hr/ml.
Figure 7B:
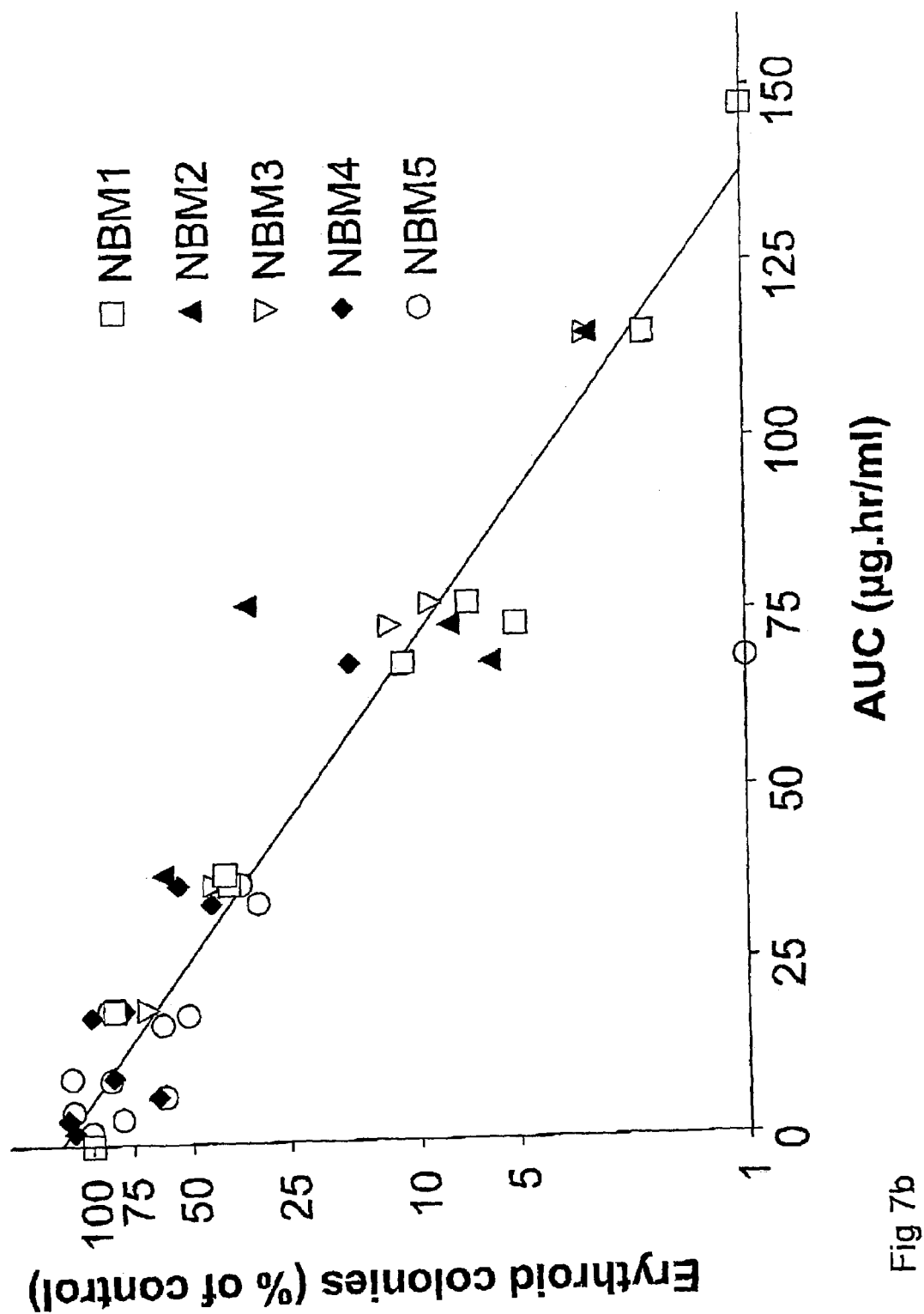
FIG. 7b. Surviving fraction of erythroid colonies related to AUC. CD34+ cells were separated from five healthy volunteers, incubated with busulphan and plated in methylcellulose medium. Erythroid colonies were counted on day 14. Results are expressed as a percentage of control. Compact line represents linear regression on all points. AUC is expressed as μg.hr/ml.

Busulphan-inhibited colony formation of CD34+ cells was AUC-dependent and linear both for CFU-GM and erythroid colonies (FIGS. 7a and 7b). The sensitivity of CFU-GM was twice as high as the sensitivity of erythroid colonies, expressed as I-$AUC_{50}$ (AUC inhibiting colony formation by 50%) or I-$AUC_{100}$ (AUC completely inhibiting colony formation). Inhibitory concentrations are presented in Table 7.

TABLE 7

AUC of busulphan (µg · hr/ml) inhibiting colony formation of normal CD34+ hematopoietic progenitor cells

|  | CFU-GM | | Erythroid colonies | |
| --- | --- | --- | --- | --- |
|  | I-$AUC_{50}$ | I-$AUC_{100}$ | I-$AUC_{50}$ | I-$AUC_{100}$ |
| BM 1 | 15.27 | 74.14 | 24.68 | 137.77 |
| BM 2 | 9.78 | 69.46 | 30.12 | 151.76 |
| BM 3 | 7.36 | 74.38 | 26.96 | 150.32 |
| BM 4 | 9.92 | 69.33 | 31.54 | 179.01 |
| BM 5 | 10.71 | 56.01 | 18.13 | 82.45 |
| Mean | 10.61 | 68.66 | 26.29 | 140.26 |
| SD | 2.89 | 7.48 | 5.29 | 35.65 |

BM = bone marrow
CFU-GM = colony forming-unit granulocyte-macrophage
I-$AUC_{50}$ = AUC inhibiting colony formation by 50%
I-$AUC_{100}$ = AUC inhibiting colony formation by 100%

Figure 8A:
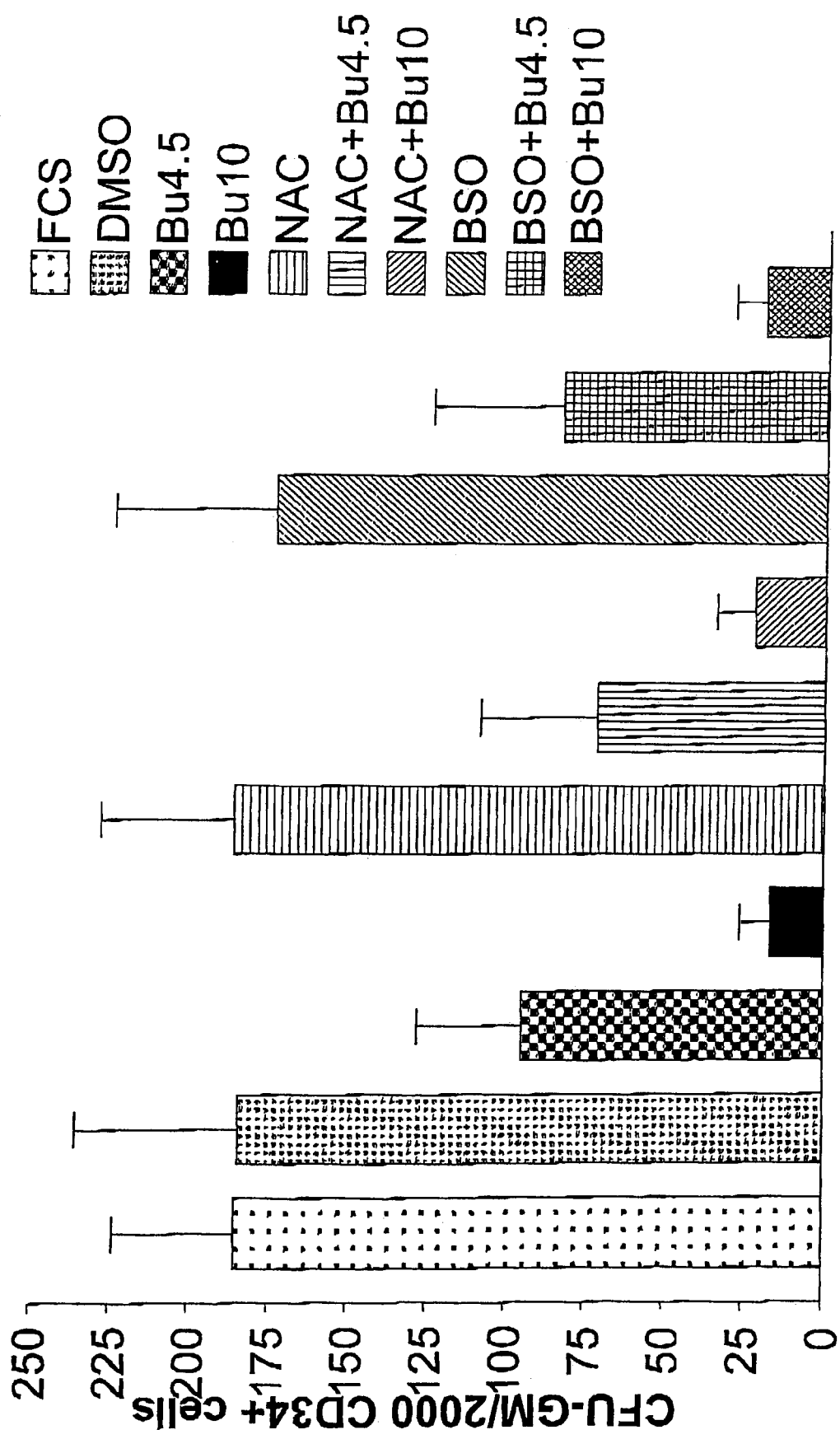
FIG. 8a. Effect of modulation of GSH intracellular content on busulphan-induced toxicity to CFU-GM. CD34+ cells were pretreated with N-acetylcysteine or buthionine sulfoximine overnight, than incubated with busulphan for 4 hours and plated in methylcellulose medium. CFU-GM were counted on day 14. Concentrations of busulphan are in μg/ml. Bars represent mean and standard deviation of 5 healthy volunteers.
Figure 8B:
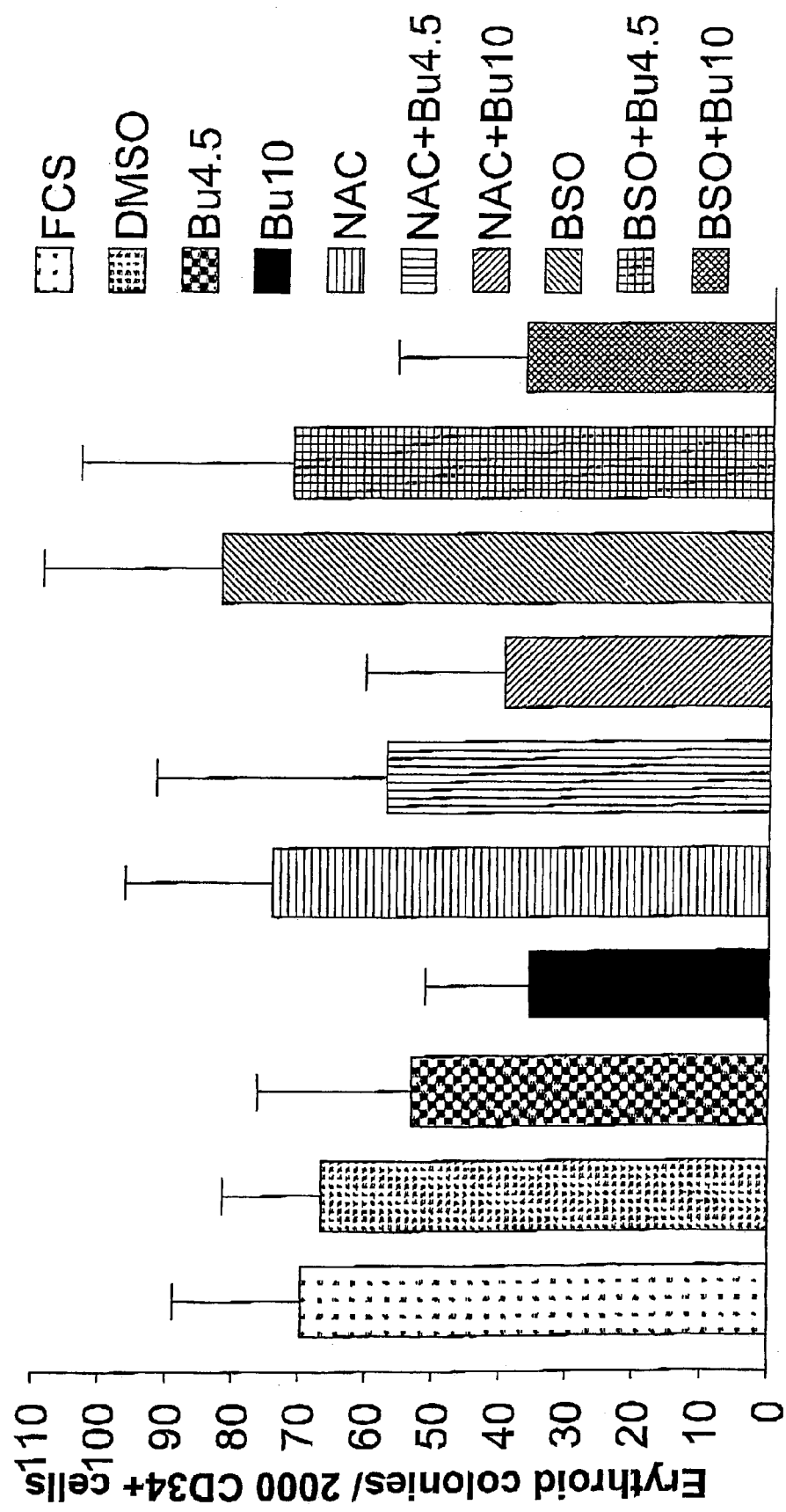
FIG. 8b. Effect of modulation of GSH intracellular content on busulphan-induced toxicity to erythroid colonies. CD34+ cells were pretreated with N-acetylcysteine or buthionine sulfoximine overnight, than incubated with busulphan for 4 hours and plated in methylcellulose medium. Erythroid colonies were counted on day 14. Concentrations of busulphan are in μg/ml. Bars represent mean and standard deviation of 5 healthy volunteers.

Modulation of GSH and its Effect on Busulphan-Induced Cytotoxicity in CD34+ Cells In Vitro Preincubation of CD34+ cells with NAC increased the GSH intracellular content to 150±30% and preincubation with BSO decreased the GSH concentration to 50±9%, compared to CD34+ cells incubated in medium (GSH 0.95±0.28 nmol/million CD34+ cells). NAC incubation did not affect busulphan-induced inhibition of colony formation of CFU-GM or erythroid colonies. Neither did preincubation of CD34+ cells with BSO change busulphan-induced inhibition of clonogenic growth. NAC or BSO alone did not influence the colony formation of CFU-GM or erythroid colonies from CD34+ cells. FIG. 8 represents the results for CFU-GM and similar results were obtained for erythroid colonies (FIGS. 8a and 8b).

Figure 9A:
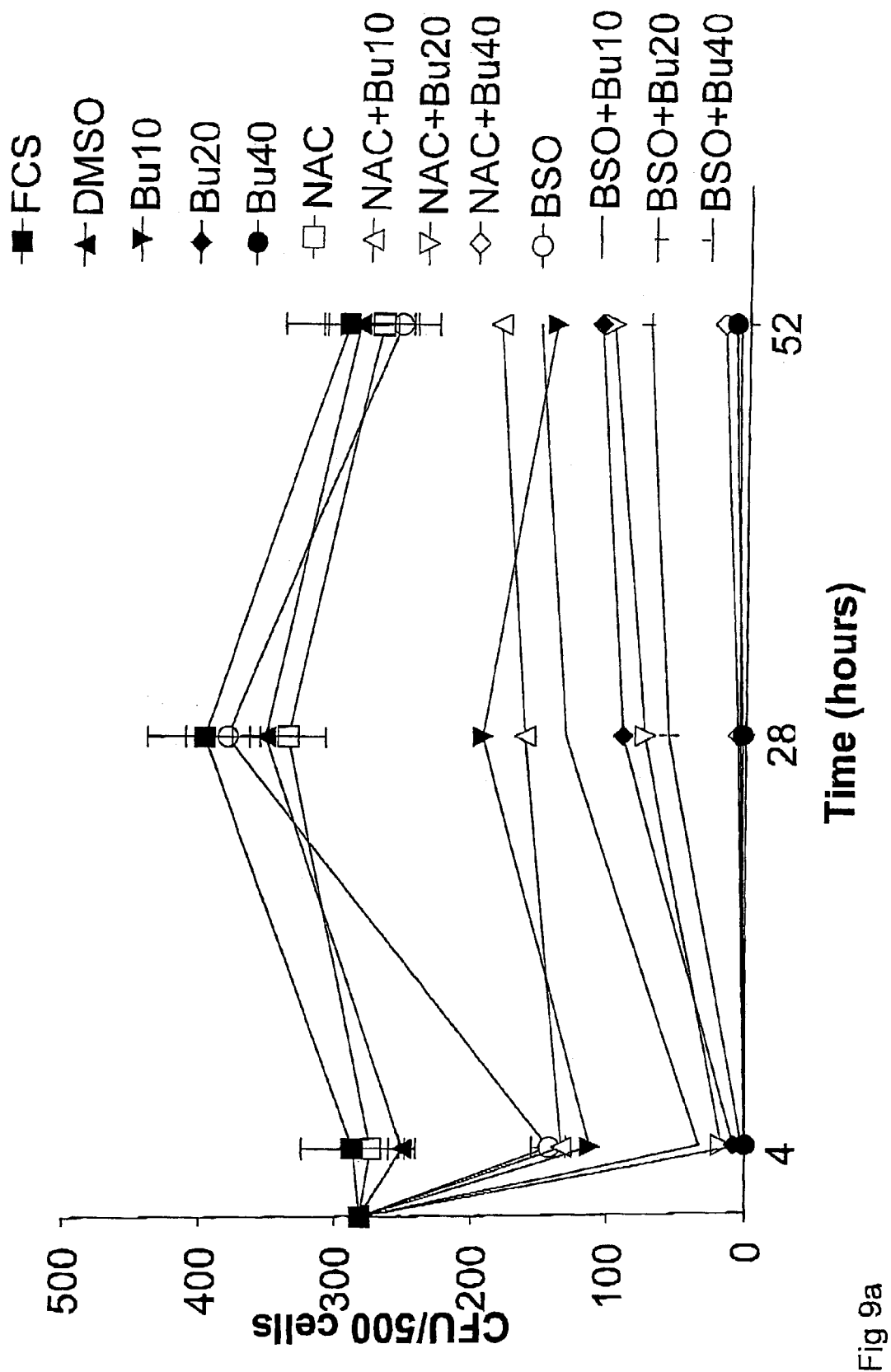
FIG. 9a. Effect of modulation of intracellular content of GSH on busulphan-induced toxicity in the myeloid P39 cells line. P39 cells were pretreated with N-acetylcysteine or buthionine sulfoximine overnight, than incubated with busulphan for 4 hours and plated in methylcellulose medium. Concentrations of busulphan are in μg/ml.
Figure 9B:
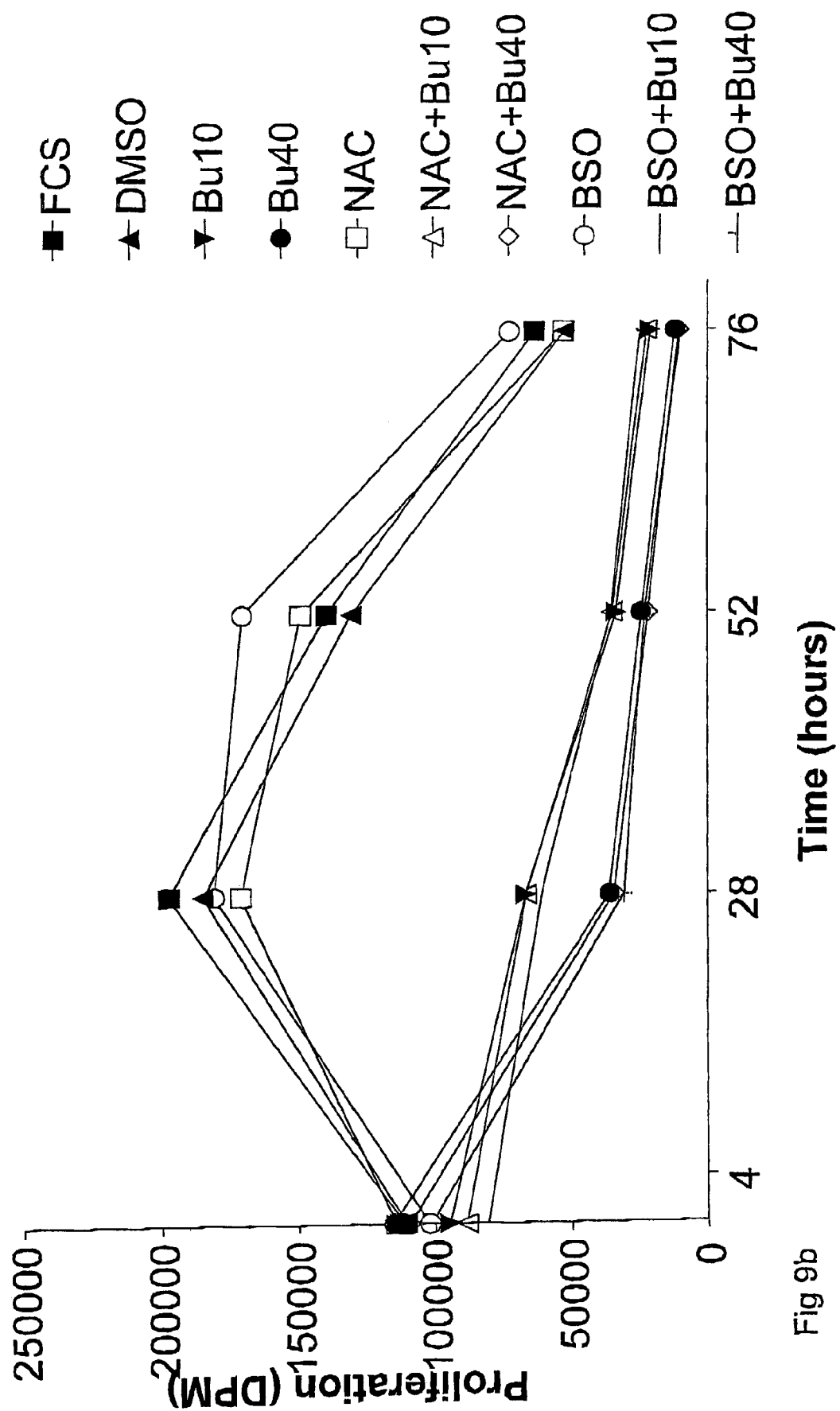
FIG. 9b. Effect of changes of intracellular content of GSH on busulphan-induced toxicity in the myeloid P39 cells line. P39 cells were pretreated with N-acetylcysteine or buthionine sulfoximine overnight, than incubated with busulphan for 4 hours and then incubated in busulphan-free medium. Proliferation was assayed as $^3$H-thymidine incorporation. Concentrations of busulphan are in μg/ml. Results represent mean from two independent experiments.

Modulation of GSH and its Effect on Busulphan-Induced Cytotoxicity in the Myeloid P39 Cell Line Preincubation of P39 cells with NAC increased the GSH intracellular level with 10% and preincubation with BSO decreased GSH with 80% compared to cells cultured in medium (GSH 4.92 nmol/million cells). Modulation of GSH did not influence the proliferation of busulphan treated cells, assessed with [$^3$H]thymidine incorporation assay (FIG. 9). As for CD34+ progenitors, neither NAC nor BSO influenced the effect of busulphan on clonogenic capacity of P39 cells (FIG. 9a). Modulation of GSH did not influence the proliferation of busulphan treated cells, assessed with [$^3$H]thymidine incorporation assay (FIG. 9b). Pretreatment of P39 cells with NAC or BSO did not change the levels of apoptosis induced by busulphan (data not shown). However, BSO alone decreased the clonogenic capacity of P39 cells by 50% immediately at the end of incubation, but the cells fully recovered after 24 hours in BSO-free media. Additive effect of BSO and busulphan in concentration of 10 μg/ml was observed immediately after the end of incubation. However, no such additive effect was observed at later time points or in higher concentrations of busulphan with recovery within 24 hours in drug-free media. Pretreatment of P39 cells with NAC or BSO did not change the levels of apoptosis induced by busulphan (data not shown).

Figure 10:
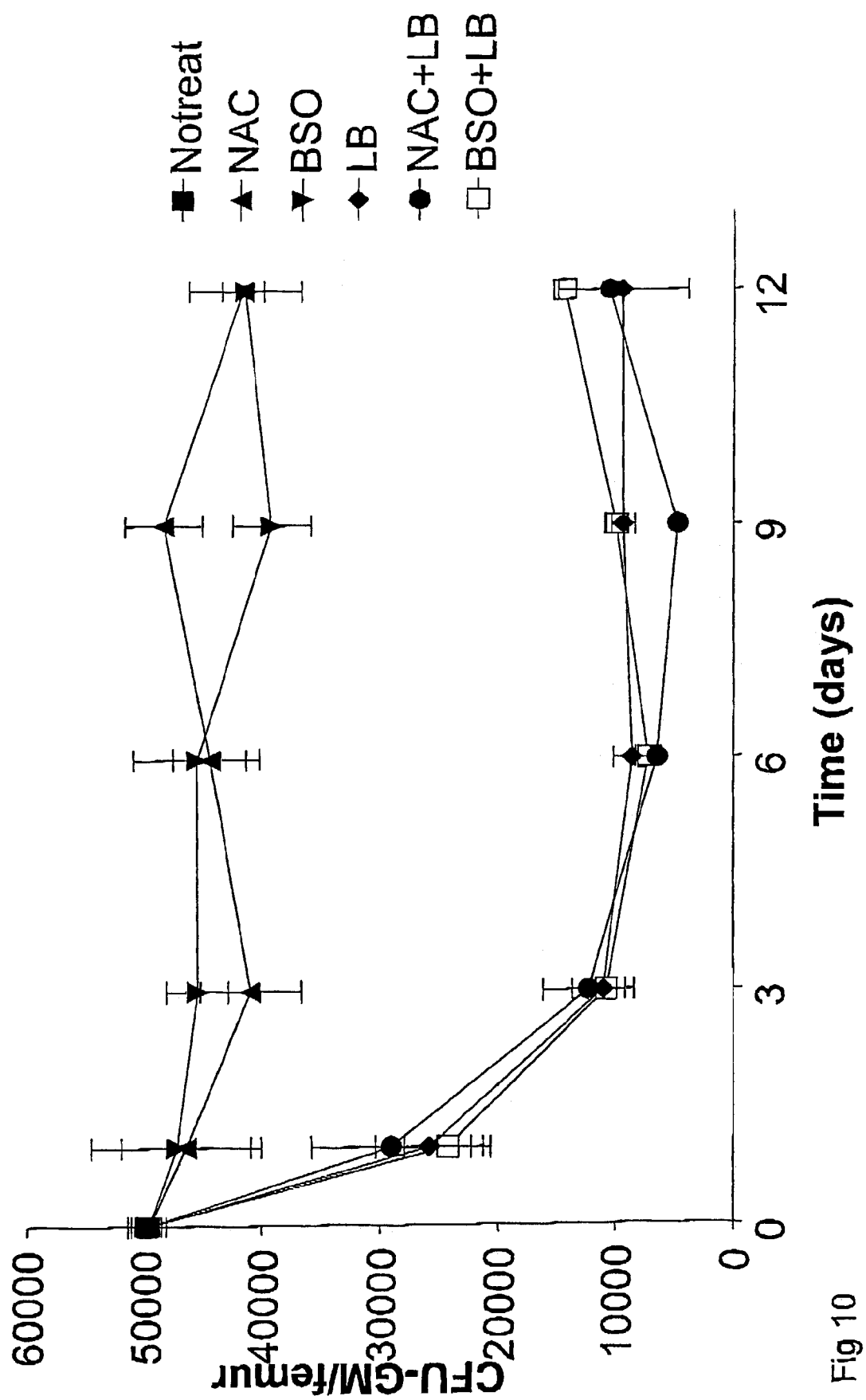
FIG. 10. Effect of pretreatment with N-acetylcysteine or buthionine sulfoximinine on busulphan-induced myelosuppression in vivo. Mice were treated once a day for four consecutive days with N-acetylcysteine or buthionine sulfoximine followed by busulphan administration. Bone marrow was harvested on day 1, 3, 6, 9 and 12 after the last dose of treatment. Nucleated cells were plated in methylcellulose medium and CFU-GM were counted on day 7. Each point represents mean ±standard deviation of minimum of three animals for treatment groups and fifteen animals for the control group.

Effect of Treatment with GSH Modulators on Busulphan-Induced Myelosuppression in Mice Busulphan induced stable myelosuppression on days 3 through 12 as assayed with CFU-GM colony-formation assay. Combination of NAC with busulphan did not significantly influence the myelosuppressive effect of busulphan. Treatment of mice with BSO and busulphan did not change the level of myelosuppression compared to animals treated with busulphan alone. Neither NAC nor BSO influenced the CFU-GM formation compared to the control group. Data are presented in FIG. 10.

Similarly, it appeared that NAC did not decrease busulphan-induced myelotoxicity in mice. Lack of protection of murine bone marrow cells in vivo by NAC has been reported also for other drugs, such as cyclophosphamide, doxorubicin or cis-dichlorodiammineplatinum(II) (Lerza, R., Bogliolo, G., Muzzulini, C., and Pannacciulli, I. Failure of N-acetyl-cysteine to protect against cis-dichlorodiammineplatinum (II)-induced hematopoietic toxicity in mice. Life Sci, 38: 1795-1800., 1986; Massa, G., Muzzulini, C., Bogliolo, G., and Pannacciulli, I. The effect of N-acetylcysteine on toxicity of cyclophosphamide and doxorubicin on murine hemopoietic progenitors. Life Sci, 36: 1141-1147., 1985). On the other hand there are many examples that the addition of NAC to the chemotherapy can alter the cytotoxic effect of the drug.

To corroborate that GSH is not involved in busulphan-induced myelotoxicity the effect of GSH depletion by BSO on busulphan-induced cytototoxicity was investigated. GSH was depleted to 50% in CD34+ cells and this level of GSH should not induce endogenous oxidative stress to cells and only an additive effect to busulphan toxicity could be expected. However, no additive effect of BSO to busulphan-induced toxicity was observed in CD34+ cells. Treatment of mice with BSO preceding the treatment with busulphan did not influence the myelosuppressive effect of busulphan within the time interval studied. GSH depletion is known to increase the effect of alkylating agents in many cell types and animal models and GSH depletion was shown to increase busulphan toxicity in hepatocytes in vitro (Mulder, G. J. and Ouwerkerk-Mahadevan, S. Modulation of glutathione conjugation in vivo: how to decrease glutathione conjugation in vivo or in intact cellular systems in vitro. Chem Biol Interact, 105: 17-34., 1997; DeLeve, L. D. and Wang, X. Role of oxidative stress and glutathione in busulfan toxicity in cultured murine hepatocytes. Pharmacology, 60: 143-154., 2000). However, no additive effect to busulphan-induced growth delay and tumour regression in human glioblastoma multiforme xenograft was observed (Hare, C. B., Elion, G. B., Colvin, O. M., Ali-Osman, F., Griffith, O. W., Petros, W. P., Keir, S., Marcelli, S. L., Bigner, D. D., and Friedman, H. S. Characterization of the mechanisms of busulfan resistance in a human glioblastoma multiforme xenograft. Cancer Chemother Pharmacol, 40: 409-414, 1997).

No effect on busulphan-induced cytotoxicity of increased GSH levels in the myeloid P39 cells was observed. However, some additive toxicity was observed when P39 cells were depleted in GSH and treated with busulphan which is probably due to decreased protection against endogenously increased oxidative stress.

In conclusion, the pharmacodynamic effect of busulphan was linear in human CD 34+ progenitor cells as well as in a leukemic cell line. Modulation of GSH cellular content did not affect busulphan-induced cytotoxicity in hematopoietic stem cells, in a leukemic cell line or in mice bone marrow.

Example 12

N-Acetyl-L-cysteine Therapy During Conditioning Prior to Allogeneic Stem Cell Transplantation Ten patients at high risk of VOD were given prophylactic treatment with NAC during pretransplant conditioning.

Patients and Methods

Patients

Ten patients, who underwent allogeneic stem cell transplantation (SCT) were included in the study. Six patients were transplanted with stem cells from matched unrelated donors, three with stem cells from HLA (Human Leukocyte Antigen) identical sibling donors and one with cord blood. The patients were included on the basis of high risk for hepatic toxicity. Eight patients (patients 1, 3, 4, 6, 7, 8, 9 and 10) had slightly to moderately elevated liver enzymes and/or bilirubin at inclusion. In two of these cases (patients 1 and 10), a previous liver biopsy had established a diagnosis of haemochromatosis. Patient 2 had an excessive busulphan blood concentration, which was also seen in patients 1 and 4. All patients had been tested negative for viral hepatitis B and C during pre-transplantation evaluation. Patient 5 had an episode of elevated liver enzymes that resolved shortly before starting conditioning. Table 8 summarizes the patient characteristics.

TABLE 8

| | | | | Patient Characteristics | | |
|---|---|---|---|---|---|---|
| Pat. No. | Sex M/F | Age mo/yrs | Donor | Stem cell source BM/PBSC | Diagnosis | VOD risk factors |
| 1 | M | 36 yrs | MUD | BM | AML M4, CR2 | Haemochromatosis and high busulphan concentration |
| 2 | M | 22 yrs | Sibling | PBSC | MDS III | High busulphan conc. |
| 3 | F | 9 mo | MUD | Cord blood | AML M5, CR1 | Hepatic toxicity NUD |
| 4 | M | 45 yrs | MUD | BM | MDS I, del 5q | Hepatic toxicity NUD |

TABLE 8-continued

Patient Characteristics

| Pat. No. | Sex M/F | Age mo/yrs | Donor | Stem cell source BM/PBSC | Diagnosis | VOD risk factors |
|---|---|---|---|---|---|---|
| 5 | M | 39 yrs | Sibling | PBSC | AML M1, CR1 | and high busulphan conc. Hepatic toxicity NUD |
| 6 | F | 6 yrs | MUD | BM | Secondary MDS IV | Hepatic toxicity NUD |
| 7 | M | 44 yrs | MUD | PBSC | AML M2, CR2 | Hepatic toxicity NUD |
| 8 | M | 40 yrs | MUD | PBSC | CML Ph+, CP1 | Hepatic toxicity NUD and high busulphan conc. |
| 9 | M | 22 yrs | Sibling | BM | Megakaryocytic aplasia | Hepatic toxicity NUD |
| 10 | M | 33 yrs | MUD | PBSC | AML M2, CR1 | Haemochromatosis |

MUD = Matched Unrelated Donor, BM = Bone Marrow, PBSC = Peripheral Blood Stem Cells, NUD = Non Ultra Descripta Treatment of Busulphan and NAC Six patients (patients 1, 2, 4, 5, 7 and 8) were conditioned with oral busulphan given during four days and cyclophosphamide 60 mg/kg/day given during two days. The initial busulphan dose given to these patients was 4 mg/kg/day. Busulphan was given twice daily. In cases of high busulphan serum concentrations the dose was reduced during conditioning as described below. Two patients (patient 3 and 6) received liposomal busulphan divided into eight doses during four days, (total dose 500 mg/m$^2$) and cyclophosphamide as described for the previous group. Patient ten received reduced conditioning with busulphan, 4 mg/kg/day, given during two days and fludarabine 30 mg/m$^2$/day during six days. Patient nine received cyclophosphamide 50 mg/kg/day during four days. Nine patients were given NAC during conditioning with busulphan. Treatment with NAC was given once daily as a three-hour infusion, 100 mg per kg body weight starting six hours after the previous busulphan dose and ending three hours before the following dose. The number of NAC doses given during and after busulphan treatment among the patients is described in Table 9. Treatment with NAC was stopped at least 12 hours before cyclophosphamide treatment. When restarted, NAC was administered not earlier than twelve hours after the end of cyclophosphamide infusion. The treatment was continued until elevated liver transaminases were normalized or, if normal transaminases at initiation of therapy, until conditioning was completed.

TABLE 9

N-Acetyl-L-Cysteine Dosing

| Pat. No | Days of acetylcysteine treatment during + after conditioning | Dose schedule | Dose |
|---|---|---|---|
| 1 | 1 + 25 | Given between busulphan and cyclophosphamide; restarted 38 hours after conditioning. | 50 mg/kg twice daily |
| 2 | 1 + 0 | Given between busulphan doses. | 100 mg/kg once daily |
| 3 | 4 + 40 | Given between busulphan doses, between busulphan and cyclophosphamide, and from day +1 after transplantation. | 100 mg/kg once daily |
| 4 | 3 + 5 | Given between busulphan doses, between busulphan and cyclophosphamide, and after conditioning. | 100 mg/kg once daily |
| 5 | 1½ + 0 | Given between busulphan and cyclophosphamide. | 50 mg/kg twice daily |
| 6 | 4 + 0 | Given between busulphan doses, between busulphan and cyclophosphamide. | 3 × 100 mg/kg once daily 1 × 50 mg/kg twice daily |
| 7 | 4 + 14 | Given between busulphan doses, between busulphan and cyclophosphamide, and after conditioning. | 100 mg/kg once daily |
| 8 | 4 + 9 | Given between busulphan doses, between busulphan and cyclophosphamide, and after conditioning. | 100 mg/kg once daily |

TABLE 9-continued

N-Acetyl-L-Cysteine Dosing

| Pat. No | Days of acetylcysteine treatment during + after conditioning | Dose schedule | Dose |
|---|---|---|---|
| 9 | 5 + 6 | Given as a 3-hour infusion starting four hours before and six hours after each cyclophosphamide dose. | 100 mg/kg twice daily on day −3 and −2, otherwise 100 mg/kg once daily |
| 10 | 7 + 12 | Given between busulphan and between fludarabine doses. | 100 mg/kg |

Busulphan Levels Determination

Busulphan was determined using gas chromatography with electron capture detector. Internal standard (1,5-bis(methanesulphonyloxy)pentane) was added to 0.5 ml plasma. Busulphan and internal standard were converted to 1,4-diiodobutane and 1,5-diiodopentane, respectively. The AUC's for each patient were measured after the oral administration using limited sampling model (based on three time points) 1, 3 and 6 hours while for the liposomal busulphan samples were collected at eleven points of time for pharmacokinetic analysis.

Patient Care

Tissue typing, conditioning, GVHD prophylaxis and infectious prophylaxis were performed as generally known to the skilled person. In short, the patients were treated in reversed isolation, immunosuppression consisted of four doses of methotrexate combined with cyclosporine and antithymocyte globuline, (Thymoglobulin, Sangstadt, Lyon, France), was given to recipients of unrelated stem cells.

Results

The Course of Transplantation: Liver Function, VOD, Neutropenia, Chimerism, and Outcome All patients with elevated liver transferases at the initiation of the NAC treatment had less elevated test results after treatment. From Table 10 it may be observed that all but one patient had completely normalized transferases. None of the patients developed VOD or fatal liver toxicity. Neutropenia developed in all patients. The leukopenia (WBC<0,5×10$^9$/L) lasted a median of 13 days (range 5-24 days).

TABLE 10

Liver enzymes and bilirubin

| | Before NAC therapy | | | After conditioning | | | After NAC therapy | | |
|---|---|---|---|---|---|---|---|---|---|
| Pat. No. | AST ukat/L | ALT ukat/L | Bilirubin umol/L | AST ukat/L | ALT ukat/L | Bilirubin umol/L | AST ukat/L | ALT ukat/L | Bilirubin umol/L |
| 1 | 0.96 | 2.25 | 5 | 1.50 | 3.45 | 12 | 0.33 | 1.19 | 19 |
| 2 | 0.38 | 0.59 | 8 | 0.40 | 0.78 | 11 | 0.42 | 0.61 | 7 |
| 3 | 11.2 | 8.10 | 3 | 0.82 | 2.24 | 6 | 0.49 | 0.52 | 6 |
| 4 | 0.85 | 1.51 | 4 | 1.76 | 4.11 | 4 | 0.29 | 0.77 | 9 |

NAC = N-acetyl-L-cysteine, AST = Aspartate aminotransferase (normal range <0.80), ALT = Alanine aminotransferase (normal range <0.8), bilirubin (normal range <26).

Table 11 summarizes the course of transplantation and patient outcome. Chimerism data at three months after SCT were available for five patients showing 100% donor origin of hematopoietic cells, (CD3+, Cd19+, CD45+), in peripheral blood for all these patients. The majority of patients experienced acute GVHD. One recurrence of leukemia was reported 15 months after transplantation. One patient died from acute GVHD on day 55 after SCT. The other patients have remained disease free and are alive for a median follow-up of six months (range 1-20 months).

TABLE 11

Course of transplantation and patient outcome

| Pat. No. | First day of WBC ≦0.5 × 10⁹/L | Engraftment day, WBC ≧0.5 × 10⁹/L | Chimerism at 1 month post SCT | Recurrence of the malignancy | Acute GVHD-grade and onset | Patient outcome |
|---|---|---|---|---|---|---|
| 1 | 2 | 16 | 100% donor | 15 mo after transplantation | I-skin, day +16 | |
| 2 | -2 | 12 | 100% donor | No | III-liver and intestin, day 22 | Died day +55 due to intestinal GVHD |
| 3 | 1 | 13 | 100% donor | No | No | |
| 4 | -1 | 12 | N.A. | No | No | |
| 5 | -3 | 15 | N.A. | No | III-liver and skin, day +15 | |
| 6 | 0 | 24 | N.A. | No | III-liver, day +18 | |
| 7 | 4 | 13 | 100% donor | No | I-skin, day +13 | |
| 8 | 5 | 10 | 100% donor | No | II-skin, day +10 | |
| 9 | -1 | 14 | N.A. | No | No | |
| 10 | 6 | 12 | N.A. | No | No | |

Day of SCT = day 0, WBC = white blood cell count, SCT = stem cell transplantation, GVHD = graft versus host diseases grades I-IV according to Seattle (33), N.A. = Not Available Busulphan Serum Concentrations Busulphan AUCs were compared before and after the administration of NAC and the results are listed in Table 12. Busulphan serum concentrations were not affected by NAC treatment. However, high concentrations of busulphan were found in patients no 2, 4 and 8 before starting NAC therapy. The AUC's after the first dose of busulphan were 20526, 15527 and 16122 ng.hr/ml for the three patients, respectively. The doses were reduced by 35, 15 and 30%, respectively, and the mean values of the AUC's during doses 4-8 were 11430, 10551 and 12122 ng.hr/ml, respectively. The AUC's of busuphan for these patients were not affected by NAC therapy, when these were corrected for 2 mg/kg.

TABLE 12

Busulphan serum concentrations before and after the administration of NAC

| Patient No | Before NAC Busulphan AUC (ng · hr/ml) AUC corrected for 2 mg/kg | After NAC Busulphan AUC (ng · hr/ml) AUC corrected for 2 mg/kg |
|---|---|---|
| 2 | 20526 | 19445 |
| 3 | 10667 | 12828 |
| 4 | 15527 | 14753 |
| 6 | 11741 | 10385 |
| 7 | 11900 | 12350 |
| 8 | 11122 | 15230 |
| 10 | 9494 | 10043 |

Patients 1 and 5 weere not given NAC between busulphan doses.
Patient 9 was given cyclophosphamide.
NAC = N-acetyl-L-cysteine, AUC = Area under the curve From Example 12 it appears that when patients at high risk of VOD were treated with NAC between repeated busulphan or cyclophosphamide doses and/or between busulphan and cyclophosphamide administrations, no side effects related to the NAC infusions were observed and busulphan serum concentrations were not affected. Furthermore, none of the patients developed VOD or liver failure. The increased liver transferases during conditioning were decreased or normalized in all patients Busulphan is metabolized mainly through GSH. During high dose treatment, busulphan may deplete cellular levels of GSH in the liver. In conditioning regimens, busulphan is usually followed by a high dose of cyclophosphamide, a prodrug that has to be activated through cytochrome P-450 enzymes. The activation of cyclophosphamide yields the cytotoxic metabolite 4-hydroxy cyclophosphamide (4-OHCP), which is highly reactive and can damage hepatocytes. Detoxification steps of 4-OHCP include GSH. The busulphan induced decrease of GSH in liver cells and possible accumulation of the cytotoxic metabolite 4-OHCP from cyclophosphamide may be one possible mechanism for the development of VOD observed using busulphan conditioning.

Thus, the findings according to Examples 11 and 12 give strong evidence that NAC does not in any significant way interfere with the myeloablative effect of a busulphan containing conditioning regimen.

Presently preferred embodiments of a liposomal preparation of busulphan according to the invention and method of preparing the same are as disclosed in Example 1 and 9. A presently preferred pharmaceutical composition according to the invention furthermore comprises NAC as a GSH precursor. A presently preferred embodiment of a method of treatment according to the invention comprises a total dose of busulphan of approximately 500 mg/m² of body surface and a daily dosage of NAC of approximately 200 mg/kg of body weight, given during a period extending at least over the whole period of busulphan administration.

REFERENCES CITED

Bandini, G. et al. 1994. Bone Marrow Transpl. 13: 577-581.
Bangham et al. 1965. J. Mol. Biol. 13: 238-252.
Bearman S I. The syndrome of hepatic venoocclusive disease after marrow transplantation. Blood 1995; 85: 3005.
Bearman S I, Appelbaum F R, Buckner C D, et al: Regimen-related toxicity in patients undergoing bone marrow transplantation. J Clin Oncol 6: 1562-8., 1988.
Bhagwatwar H. P, Phadungpojna S, Chow D. S, Andersson B. S. 1996. Cancer Chemother Pharmacol 37: 401.

Canellos G. P., Chronic Leukemias. In: Cancer: Principles and Practice of Oncology, $2^{nd}$ Edition. 1985, DeVita V. T. Jr et al., (Eds). J. B. Lippinicott Co. Philadelphia, Pa. pp 1739-1752.

Carreras E. Venoocclusive disease of the liver after hematopoietic cell transplantation. Eur J Haematol 2000; 64(5): 281-91.

Chattergoon D S, Saunders E F, Klein J, et al: An improved limited sampling method for individualised busulphan dosing in bone marrow transplantation in children. Bone Marrow Transplant 20: 347-54, 1997.

Chyka, P. A., Butler, A. Y., Holliman, B. J., and Herman, M. I. Utility of acetylcysteine in treating poisonings and adverse drug reactions. Drug Saf, 22: 123-148., 2000.

Crowe L M, Crowe J H, Rudolph A, Womersley C, Appel L: Preservation of freeze-dried liposomes by trehalose. Arch Biochem Biophys 1985 October; 242(1):240-7.

Czerwinski M, Gibbs J P, Slattery J T. Busulfan conjugation by glutathione S-transferase alpha, my and pi. Drug Metab Dispos 1996; 24(9): 1015-9.

De Leve L D, Wang X. Role of oxidative stress and glutathione in busulfan toxicity in cultured murine hepatocytes. Pharmacology 200; 60(3):143-54.

Dix S P, Wingard J R, Mullins R E, et al: Association of busulfan area under the curve with veno-occlusive disease following BMT. Bone Marrow Transplant 17: 225-30, 1996.

Ehninger G, Schuler U, Renner U, Ehrsam M, Zeller K. P, Blanz J, Storb R, Deeg H. J. 1995. Blood 85: 3247.

Gibbs J P, Czerwinski M, Slattery J T. Busulfan-glutathione conjugation catalyzed by human liver cytosolic glutathione S-transferases. Cancer Res 1996; 56(16):3678-81.

Glucksberg H, Storb R, Fefer A, et al: Clinical manifestations of graft-versus-host disease in human recipients of marrow from HL-A-matched sibling donors. Transplantation 18: 295-304, 1974.

Griffith, O. W. and Meister, A. Potent and specific inhibition of glutathione synthesis by buthionine sulfoximine (S-n-butyl homocysteine sulfoximine). J Biol Chem, 254: 7558-7560, 1979.

Grochow L B, Jones R J, Brundrett R B, Braine H G, Chen T L, Saral R, et al. Pharmacokinetics of busulfan: correlation with venoocclusive disease in patients undergoing bone marrow transplantation. Cancer Chemother Pharmacol 1989; 25(1): 55-61.

Hare, C. B., Elion, G. B., Colvin, O. M., Ali-Osman, F., Griffith, O. W., Petros, W. P., Keir, S., Marcelli, S. L., Bigner, D. D., and Friedman, H. S. Characterization of the mechanisms of busulfan resistance in a human glioblastoma multiforme xenograft. Cancer Chemother Pharmacol, 40: 409-414, 1997.

Hassan, M., Ehrsson, H. 1983. J Chromatogr 277: 374.

Hassan M, Ehrsson H. Metabolism of 14C-busulfan in isolated perfused rat liver. Eur J Drug Metab Pharmacokinet 1987; 12(1):71-6.

Hassan M, Fasth A, Gerritsen B, et al: Busulphan kinetics and limited sampling model in children with leukemia and inherited disorders. Bone Marrow Transplant 18: 843-50, 1996.

Hassan, Z., Hassan, M., and Hellstrom-Lindberg, E. The pharmacodynamic effect of busulfan in the P39 myeloid cell line in vitro. Leukemia, 15: 1240-1247., 2001.

Kennedy Jr G. L, Sherman H. 1986. Drug and Chemical Toxicology 9: 147. Kinney L. A, Burgess B. A, Stula E. F, Kennedy Jr G. L. 1993. Drug and Chemical Toxicology 16: 175.

Lerza, R., Bogliolo, G., Muzzulini, C., and Pannacciulli, I. Failure of N-acetylcysteine to protect against cis-dichlorodiammineplatinum(II)-induced hematopoietic toxicity in mice. Life Sci, 38: 1795-1800., 1986.

Ljungman P, Hassan M, Bekassy A N, et al: High busulfan concentrations are associated with increased transplant-related mortality in allogeneic bone marrow transplant patients. Bone Marrow Transplant 20: 909-13, 1997.

Lowry, O. H., Rosebrough, N. J., Farr, A. L., and Randall, R. J. Protein measurement with the folin phenol reagent. J Biol Chem, 193: 265-275., 1951.

Lu, C. et al. 1984. Cancer Treatm. Repts. 68: 711-717.

Malley L. A, Slone Jr T. W, Makovec G. T, Elliott G. S, Kennedy Jr G. L. 1995. Fundam Appl Toxicol 28: 80.

Marchand D H, Remmel R P, Abdel-Monem M M. Biliary excretion of a glutathione conjugate of busulfan and 1,4 diiodobutane in the rat. Drug Metab Dispos 1988; 16(1): 85-92.

Martino M, Morabito F, Messina G, Irrera G, Pucci G, Iacopino P. 1996. Haematologica 81: 59.

Massa, G., Muzzulini, C., Bogliolo, G., and Pannacciulli, I. The effect of N-acetylcysteine on toxicity of cyclophosphamide and doxorubicin on murine hemopoietic progenitors. Life Sci, 36: 1141-1147., 1985.

Meister A. Glutathione metabolism and its selective modification. J Biol Chem 1988; 263(33): 17205-8.

Miller, C. et al. 1991. Blood 78: 1155.

Mulder, G. J. and Ouwerkerk-Mahadevan, S. Modulation of glutathione conjugation in vivo: how to decrease glutathione conjugation in vivo or in intact cellular systems in vitro. Chem Biol Interact, 105: 17-34, 1997.

Oakhill et al. 1981. J. Clin. Pathol. 34(5):495-500.

Papahadjopoulos et al. Biochim. Biophys. Acta. 1967. 135: 624-638.

Pawlowska A B, Blazar B R, Angelucci E, et al: Relationship of plasma pharmacokinetics of high-dose oral busulfan to the outcome of allogeneic bone marrow transplantation in children with thalassemia. Bone Marrow Transplant 20: 915-20, 1997.

Ringden, O., Remberger, M., Lehmann, S., Hentschke, P., Mattsson, J., Klaesson, S., Aschan, J.: N-acetylcysteine for hepatic veno-occlusive disease after allogeneic stem cell transplantation. Bone Marrow Transplant. 25: 993-996, 2000.

Ringdén O, Remberger M, Ruutu T, et al: Increased risk of chronic graft-versus-host disease, obstructive bronchiolitis, and alopecia with busulfan versus total body irradiation: long-term results of a randomized trial in allogeneic marrow recipients with leukemia. Nordic Bone Marrow Transplantation Group. Blood 93: 2196-201, 1999.

Ringden O, Ruutu T, Remberger M, et al. A randomised trial comparing busulfan with total body irradiation as conditioning in allogeneic marrow transplant recipients with leukemia: A report from the Nordic Bone Marrow Transplant Group. Blood 1994; 83: 2723-2730.

Ritter C A, Bohnenstengel F, Hofmann Um Kroemer H K, Sperker B. Determination of tetrahydrothiophene formation as a probe of in vitro busulfan metabolism by human glutathione S-transferase A1-1: use of a highly sensitive gas chromatographic-mass spectrometric method. J Chromatogr B Biomed Sci Appl 1999; 730(1):25-31.

Rudolph A S: The freeze-dried preservation of liposome encapsulated hemoglobin: a potential blood substitute. Cryobiology 1988 Aug., 25(4):277-84

Santos, G. W. et al. 1983. N. Engl. J. Med. 309: 1347-1353.

Schuler et al. 1997. Abstract EBMT-meeting, Chamonix, France.

Schuler U, Schroer S, Kuhnle A, et al: Busulfan pharmacokinetics in bone marrow transplant patients: is drug monitoring warranted? Bone Marrow Transplant 14: 759-65, 1994.

Selig, C., Nothdurft, W., and Fliedner, T. M. Radioprotective effect of N-acetylsysteine on granulocyte/macrophage colony-forming cells of human bone marrow. J Cancer Res Clin Oncol, 119: 346-349, 1993.

Shulman H M, Hinterberger W. Hepatic venooccusive disease—liver toxicity syndrome after bone marrow transplantation. Transplantation 1992; 10: 197.

Slattery J T, Sanders J E, Buckner C D, et al: Graft-rejection and toxicity following bone marrow transplantation in relation to busulfan pharmacokinetics [published erratum appears in Bone Marrow Transplant 1996 October; 18(4): 829]. Bone Marrow Transplant 16: 31-42, 1995.

Sperling S, Larsen I. G. 1979. Acta Opthalmol (Copenh) 57: 891.

Tietze, F. Enzymic method for quantitative determination of nanogram amounts of total and oxidized glutathione: applications to mammalian blood and other tissues. Anal Biochem, 27: 502-522., 1969.

U.S. Pat. No. 5,430,057

U.S. Pat. No. 5,559,148

Vassal G, Deroussent A, Challine D, et al: Is 600 mg/m2 the appropriate dosage of busulfan in children undergoing bone marrow transplantation? Blood 79: 2475-9, 1992.

Vassal G, Deroussent A, Hartmann O, et al: Dose-dependent neurotoxicity of high-dose busulfan in children: a clinical and pharmacological study. Cancer Res 50: 6203-7, 1990.

Weiner et al: Lipsomes as a Drug Deliver System, Drug Development and Industrial Pharmacy, 15(10), 1523-1554.

Yellowlees P, Greenfield C, McIntyre N. 1980. Lancet 2: 1004.

The invention claimed is:

1. A liposome composition for myelosuppressive treatment comprising
busulphan encapsulated in liposomes having a size of from 50 to 300 nm;
said liposome composition having a character that, when administered to a mammalian patient, does not accumulate in the patient's liver;
said liposomes having membranes comprising lipids,
wherein the lipids are L-α-phosphatidylcholine, 1,2-dioleoyl-sn-glycero-3-phosphate and cholesterol,
said lipids being present in a molar ratio of about 9.45:1:9.4.

2. A liposome composition for myelosuppressive treatment comprising
busulphan encapsulated in liposomes having a size of from 50 to 300 nm;
said liposome composition having a character that, when administered to a mammalian patient, does not accumulate in the patient's liver;
said liposomes having membranes comprising lipids,
wherein the lipids are at least one of phosphatidylserine, phosphatidylcholine and cholesterol,
said lipids being present in a molar ratio of about 3:7:10.

3. A liposome composition for myelosuppressive treatment comprising
busulphan encapsulated in liposomes having a size of from 50 to 300 nm;
said liposome composition having a character that, when administered to a mammalian patient, does not accumulate in the patient's liver;
said liposomes having membranes comprising lipids,
wherein the lipids are cardiolipin, phosphatidylcholine and cholesterol,
said lipids being present in a molar ratio of about 1:4:1.5.

4. A liposome composition for myelosuppressive treatment comprising
busulphan encapsulated in liposomes having a size of from 50 to 300 nm;
said liposome composition having a character that, when administered to a mammalian patient, does not accumulate in the patient's liver;
said liposomes having membranes comprising lipids,
wherein the lipids are phosphatidylcholine, cholesterol and stearylamine,
said lipids being present in a molar ratio of about 7:1:1.

5. A pharmaceutical composition comprising a liposome composition according to claim 1 and a pharmaceutically acceptable carrier.

6. A pharmaceutical composition according to claim 5, further comprising glutathione (GSH) and/or at least one GSH precursor compound that through cellular reactions within the body of a mammal is transformed into GSH, and
wherein the GSH precursor compound is selected from the group consisting of N-acetylcysteine, methionine, cysteine, glutamine, cystine, homocysteine, glycine, cysteinylglycine, glutamyl aminoacid, and glutamyl cysteine.

7. A pharmaceutical composition according to claim 6, wherein the GSH precursor compound is N-acetylcysteine.

8. A method of treating a mammalian patient in need of myelosuppressive treatment comprising parenterally administering to the patient an effective amount of a pharmaceutical composition according to claim 5.

9. The method according to claim 8, further comprising administering to the mammalian patient during a period at least partly overlapping with the period of myelosuppressive treatment, a pharmaceutical composition comprising GSH and/or at least one GSH precursor compound that through intracellular reactions within the body of the mammal is transformed into GSH, in a pharmaceutically acceptable carrier,
wherein the GSH precursor compound is selected from N-acetylcysteine, methionine, cysteine, glutamine, cystine, homocysteine, glycine, cysteinylglycine, glutamyl aminoacid, glutamyl cysteine.

10. The method according to claim 8, wherein the mammalian patient is undergoing a stem cell or bone marrow transplantation.

11. A method of treating a mammalian patient in need of myelosuppressive treatment comprising parenterally administering to the patient an effective amount of a pharmaceutical composition according to claim 6.

12. A liposome composition according to claim 1 in a dehydrated state.

13. A liposome composition according to claim 1 in a lyophilized state.

14. The method according to claim 9, wherein said period of administration of composition comprising GSH and/or at least one GSH precursor compound extends over the entire period of myelosuppressive treatment.

15. A pharmaceutical composition comprising a liposome composition according to claim 2 and a pharmaceutically acceptable carrier.

16. A pharmaceutical composition comprising a liposome composition according to claim 3 and a pharmaceutically acceptable carrier.

17. A pharmaceutical composition comprising a liposome composition according to claim 4 and a pharmaceutically acceptable carrier.

18. A pharmaceutical composition according to claim 15, further comprising glutathione (GSH) and/or at least one GSH precursor compound that through cellular reactions within the body of a mammal is transformed into GSH, and
    wherein the GSH precursor compound is selected from the group consisting of N-acetylcysteine, methionine, cysteine, glutamine, cystine, homocysteine, glycine, cysteinylglycine, glutamyl aminoacid, and glutamyl cysteine.

19. A pharmaceutical composition according to claim 16, further comprising glutathione (GSH) and/or at least one GSH precursor compound that through cellular reactions within the body of a mammal is transformed into GSH, and
    wherein the GSH precursor compound is selected from the group consisting of N-acetylcysteine, methionine, cysteine, glutamine, cystine, homocysteine, glycine, cysteinylglycine, glutamyl aminoacid, and glutamyl cysteine.

20. A pharmaceutical composition according to claim 17, further comprising glutathione (GSH) and/or at least one GSH precursor compound that through cellular reactions within the body of a mammal is transformed into GSH, and
    wherein the GSH precursor compound is selected from the group consisting of N-acetylcysteine, methionine, cysteine, glutamine, cystine, homocysteine, glycine, cysteinylglycine, glutamyl aminoacid, and glutamyl cysteine.

\* \* \* \* \*